United States Patent [19]

Hayashi et al.

[11] Patent Number: 4,708,734

[45] Date of Patent: Nov. 24, 1987

[54] 5-(2-CHLORO-4-TRIFLUOROMETHYL-PHENOXY)-2-NITRO-α-SUBSTITUTED-ACETOPHENONE, OXIME DERIVATIVE THEREOF, HERBICIDAL COMPOSITION, AND METHOD FOR THE DESTRUCTION OF UNDESIRABLE WEEDS

[75] Inventors: Yoshiharu Hayashi; Teruyuki Misumi, both of Yokohama, Japan

[73] Assignee: Asahi Kasei Kogyo Kabushiki Kaisha, Osaka, Japan

[21] Appl. No.: 807,799

[22] Filed: Dec. 11, 1985

[30] Foreign Application Priority Data

Dec. 12, 1984 [JP] Japan .................................. 59-262165
Feb. 21, 1985 [JP] Japan .................................. 60-31604
May 9, 1985 [JP] Japan .................................. 60-96611
Jun. 10, 1985 [JP] Japan .................................. 60-124365
Jul. 15, 1985 [JP] Japan .................................. 60-154285

[51] Int. Cl.$^4$ ...................... A01N 37/00; C07C 79/46; C07C 101/00; C07C 81/08
[52] U.S. Cl. .......................... 71/100; 71/106; 71/113; 558/251; 558/253; 558/252; 558/255; 558/254; 560/21; 560/35; 562/435; 562/463; 568/331; 564/258
[58] Field of Search ............... 558/251, 253, 252, 255, 558/254; 560/21, 35; 562/435, 463; 71/100, 106, 113; 568/331; 564/258

[56] References Cited

U.S. PATENT DOCUMENTS 3,184,510 5/1965 Levy .................................. 564/256
4,344,789 8/1982 Krass .................................. 71/100
4,401,602 8/1983 Krass .................................. 71/100
4,490,167 12/1984 Pissiotas et al. ...................... 71/100

FOREIGN PATENT DOCUMENTS 0155613 9/1985 European Pat. Off. .............. 560/21

OTHER PUBLICATIONS

Noller, Textbook of Organic Chemistry, W. B. Saunders Company, Philadelphia, Pa., 1966, pp. 204, 375.

*Primary Examiner*—Richard A. Schwartz
*Assistant Examiner*—Robert C. Whittenbaugh
*Attorney, Agent, or Firm*—Birch, Stewart, Kolasch and Birch

[57] ABSTRACT

5-2-chloro-4-trifluoromethylphenoxy)-2-nitro-α-substituted-acetophenones and oxime derivatives thereof represented by the formula

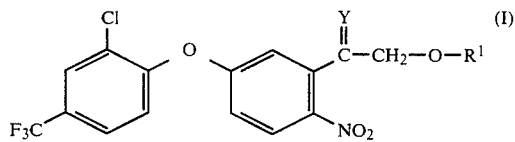

wherein R$^1$ and Y are as defined in the disclosure, process for the preparation thereof, herbicidal composition and method for the destruction of undesirable weeds. The herbicides comprising the above compounds are capable of selectively controlling undesirable weeds among desirable crop plants.

45 Claims, No Drawings

4,708,734

5-(2-CHLORO-4-TRIFLUOROMETHYLPHENOXY)-2-NITRO-α-SUBSTITUTED-ACETOPHENONE, OXIME DERIVATIVE THEREOF, HERBICIDAL COMPOSITION, AND METHOD FOR THE DESTRUCTION OF UNDESIRABLE WEEDS

FIELD OF THE INVENTION

This invention relates to a novel compound which exhibits a high herbicidal activity with high selectivity, a novel process for the preparation thereof, a novel herbicidal composition comprising as an active ingredient the novel compound which is useful as an effective herbicide for various crops and a method for the destruction of undesirable weeds using the novel compound. More particularly, the present invention is concerned with a 5-(2-chloro-4-trifluoromethylphenoxy)-2-nitro-α-substituted acetophenone compound and an oxime derivative thereof, a process for the preparation of such compounds, a herbicidal composition comprising such compounds and a method for the destruction of undesirable weeds using the compound.

DESCRIPTION OF THE PRIOR ART

To now, a herbicide comprising as an active ingredient an alkyl [2-nitro-5-(2-chloro-4-trifluoromethylphenoxy)phenyl] ketone compound or an oxime derivative thereof is well known as the generally called diphenyl ether type herbicide (see, for example, U.S. Pat. No. 4,344,789 and 4,401,602). Also, it is well known, as another class of the diphenyl ether type herbicide, a herbicide comprising as an active ingredient an oxime derivative of 2-nitro-5-(2-chloro-4-trifluoromethylphenoxy)phenylacetonitrile (see, U.S. Pat. No. 4,490,167).

However, with respect to all of the known diphenyl ether herbicides, there is a dilemma, that is, when they are good in herbicidal activity, they are poor in selectivity, and when they are good in selectivity, they are poor in herbicidal activity. Hence, none of them are suitable for efficient and prompt control of only undesirable species of weeds.

The ideal herbicide should be one which further satisfies the following conditions in addition to the above-stated excellent herbicidal activity and high selectivity. The toxicity of the herbicide to warmblooded animals must be low. The herbicide is effective even if it is applied any time through the whole period of growth of crop plants. Moreover, after usage, the herbicide decomposes as promptly as possible so that it does not contaminate the soil. However, such an ideal diphenyl ether herbicide which satisfies the above conditions is not yet known.

OBJECT OF THE INVENTION

Under the above-stated current situation, the inventors have made intensive studies to develop a novel diphenyl ether herbicide which is free from the drawbacks inevitably accompanying the conventional diphenyl ether herbicides, which has selective and high herbicidal activity that means complete safety to crop plants and prompt elimination of any unnecessary weeds present therewith, which can be used continuously through the whole period of growth of crop plants. As a result, it has been found that a novel 5-(2-chloro-4-trifluoromethylphenoxy)-2-nitro-α-substituted-acetophenone compound and oxime derivatives thereof satisfy the above-mentioned requirements for an improved herbicide, and that the compounds, even at a low dosage, are very effective for a wide spectrum of broad-leaved and Gramineae family crop plants, such as soybean, peanut, corn, wheat and rice plants. Based on this novel finding, the present invention has been completed.

Accordingly, it is an object of the present invention to provide a novel 5-(2-chloro-4-trifluoromethylphenoxy)-2-nitro-α-substituted-acetophenone compound and an oxime derivative thereof having a high selectivity as well as a high herbicidal activity.

It is another object of the present invention to provide a process for the preparation of the above-mentioned compounds having a highly selective herbicidal activity.

It is a further object of the present invention to provide a novel herbicidal composition containing the above-mentioned compounds.

It is still a further object of the present invention to provide a method for the destruction of undesirable weeds using the novel compound of the described above.

It is still a further object of the present invention to provide novel intermediate compounds which are useful for the preparation of the above-mentioned compounds.

The foregoing and other objects, features and advantages of the present invention will be apparent to those skilled in the art from the following detailed description and appended claims.

DESCRIPTION OF THE INVENTION

In one aspect of this invention, there is provided a compound represented by the formula

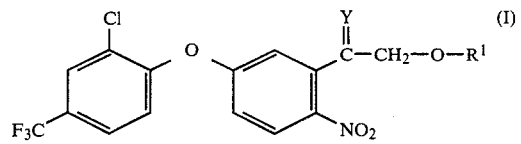

wherein
R$^1$ represents a methyl group or

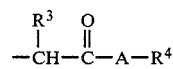

in which
A represents an oxygen atom or a sulfur atom,
R$^3$ represents a hydrogen atom or a methyl group,
and R$^4$ represents a hydrogen atom, an alkyl group having 1 to 4 carbon atoms, an alkenyl group having 3 to 6 carbon atoms, an alkynyl group having 3 to 6 carbon atoms, or an alkyl group having 1 to 4 carbon atoms and substituted with a halogen atom, an alkoxy group having 1 to 3 carbon atoms or a carboalkoxy group having 2 to 4 carbon atoms; and
Y represents an oxygen atom or =N-O-R$^2$ in which
R$^2$ represents a hydrogen atom, an alkyl group having 1 to 3 carbon atoms or

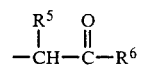

in which
R$^5$ represents a hydrogen atom or a methyl group, and $R^6$ represents $-BR^7$ or

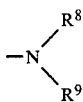

in which

B represents an oxygen atom or a sulfur atom, $R^7$ represents a hydrogen atom, an alkyl group having 1 to 4 carbon atoms, an alkenyl group having 3 to 6 carbon atoms, an alkynyl group having 3 to 6 carbon atoms, a substituted or unsubstituted phenyl group, an alkyl group having 1 to 4 carbon atoms and substituted with a halogen atom or an alkoxy group having 1 to 3 carbon atoms, an alkali metal, an alkaline earth metal in proportion corresponding to mono-valency of the alkaline earth metal, an ammonium group, an ammonium group substituted with an alkyl group having 1 to 4 carbon atoms, or

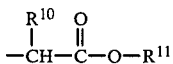

in which $R^{10}$ represents a hydrogen atom or a methyl group, and $R^{11}$ represents an alkyl group having 1 to 3 carbon atoms, and $R^8$ and $R^9$ are identical or different and each independently represent a hydrogen atom, an alkyl group having 1 to 3 carbon atoms, an alkynyl group having 3 to 6 carbon atoms, or an alkoxy group having 1 to 3 carbon atoms.

The characteristic feature of the compounds of the present invention resides in that they have, in their respective molecular structures, an α-substituted-acetophenone or an oxime derivative thereof, as opposed to the conventional similar compounds which have, in their respective molecular structures, an α-unsubstituted alkyl phenyl ketone such as acetophenone or propiophenone, an oxime derivative thereof, or an oxime derivative of phenylacetonitrile. It is surprising that the introduction of a substituent to the α-position of the acetophenone moiety enables the compounds of the present invention to provide a preemergence or postemergence herbicide which is very effective for control of undesirable weeds at a lower dosage and has a high selectivity as well as a high activity, as compared with the conventional compounds having similar structures.

The terminologies used herein for naming the present compounds, for example, 5-(2-chloro-4-trifluoromethylphenoxy)- 2-nitro-α-methoxyacetophenone oxime-O-(acetic acid, methyl ester) are intended to include syn-anti isomers and the other stereoisomers.

As specific examples of the compound of the present invention, there may be mentioned as follows.

The compounds represented by the above-mentioned formula (I) in which Y is =N-O-$R^2$ include:

5-(2-chloro-4-trifluoromethylphenoxy)-2-nitro-α-methoxyacetophenone oxime, 5-(2-chloro-4-trifluoromethylphenoxy)-2-nitro-α-methoxyacetophenone-O-methyl oxime, 5-(2-chloro-4-trifluoromethylphenoxy)-2-nitro-α-methoxyacetophenone-O-ethyl oxime, 5-(2-chloro-4-trifluoromethylphenoxy)-2-nitro-α-methoxyacetophenone-O-n-propyl oxime, 5-(2-chloro-4-trifluoromethylphenoxy)-2-nitro-α-methoxyacetophenone-O-iso-propyl oxime, 5-(2-chloro-4-trifluoromethylphenoxy)-2-nitro-α-methoxyacetophenone oxime-O-(acetic acid), sodium 5-(2-chloro-4-trifluoromethylphenoxy)-2-nitro-α-methoxyacetophenone oxime-O-acetate, potassium 5-(2-chloro-4-trifluoromethylphenoxy)--nitro-α-methoxyacetophenone oxime-O-acetate, calcium 5-(2-chloro-4-trifluoromethylphenoxy)-2-nitro-α-methoxyacetophenone oxime-O-acetate, magnesium 5-(2-chloro-4-trifluoromethylphenoxy)-2-nitro-α-methoxyacetophenone oxime-O-acetate, ammonium 5-(2-chloro-4-trifluoromethylphenoxy)-2-nitro-α-methoxyacetophenone oxime-O-acetate, methylammonium 5-(2-chloro-4-trifluoromethylphenoxy)-2-nitro-α-methoxyacetophenone oxime-O-acetate, dimethylammonium 5-(2-chloro-4-trifluoromethylphenoxy)-2-nitro-α-methoxyacetophenone oxime-O-acetate, 5-(2-chloro-4-trifluoromethylphenoxy)-2-nitro-α-methoxyacetophenone oxime-O-(acetic acid, methyl ester), 5-(2-chloro-4-trifluoromethylphenoxy)-2-nitro-α-methoxyacetophenone oxime-O-(acetic acid, ethyl ester), 5-(2-chloro-4-trifluoromethylphenoxy)-2-nitro-α-methoxyacetophenone oxime-O-(acetic acid, n-propyl ester), 5-(2-chloro-4-trifluoromethylphenoxy)-2-nitro-α-methoxyacetophenone oxime-O-(acetic acid, n-butyl ester), 5-(2-chloro-4-trifluoromethylphenoxy)-2-nitro-α-methoxyacetophenone oxime-O-(acetic acid, allyl ester), 5-(2-chloro-4-trifluoromethylphenoxy)-2-nitro-α-methoxyacetophenone oxime-O-(acetic acid, 2-methyl-2-propenyl ester), 5-(2-chloro-4-trifluoromethylphenoxy)-2-nitro-α-methoxyacetophenone oxime-O-(acetic acid, crotyl ester), 5-(2-chloro-4-trifluoromethylphenoxy)-2-nitro-α-methoxyacetophenone oxime-O-(acetic acid, propargyl ester), 5-(2-chloro-4-trifluoromethylphenoxy)-2-nitro-α-methoxyacetophenone oxime-O-(acetic acid, phenyl ester), 5-(2-chloro-4-trifluoromethylphenoxy)-2-nitro-α-methoxyacetophenone oxime-O-(acetic acid, p-methoxyphenyl ester), 5-(2-chloro-4-trifluoromethylphenoxy)-2-nitro-α-methoxyacetophenone oxime-O-(acetic acid, m-chlorophenyl ester), 5-(2-chloro-4-trifluoromethylphenoxy)-2-nitro-α-methoxyacetophenone oxime-O-(acetic acid, o-methylphenyl ester), 5-(2-chloro-4-trifluoromethylphenoxy)-2-nitro-α-methoxyacetophenone oxime-O-(acetic acid, 2-chloroethyl ester), 5-(2-chloro-4-trifluoromethylphenoxy)-2-nitro-α-methoxyacetophenone oxime-O-(acetic acid, 2-bromoethyl ester), 5-(2-chloro-4-trifluoromethylphenoxy)-2-nitro-α-methoxyacetophenone oxime-O-(acetic acid, 2,2,2-trifluoroethyl ester), 5-(2-chloro-4-trifluoromethylphenoxy)-2-nitro-α-methoxyacetophenone oxime-O-(acetic acid, 2-methoxyethyl ester), 5-(2-chloro-4-trifluoromethylphenoxy)-2-nitro-α-methoxyacetophenone oxime-O-(acetic acid, 2-ethoxyethyl ester), 5-(2-chloro-4-trifluoromethylphenoxy)-2-nitro-α-methoxyacetophenone oxime-O-(acetic acid, 1-methyl-2methoxyethyl ester), methyl 2-[[[[2-nitro-5-(2'-chloro-4'-trifluoromethylphenoxy)-α-methoxymethylbenzylidene]amino]oxy]acetoxy]acetate, ethyl 2-[[[[2-nitro-5-(2'-chloro-4'-trifluoromethylphenoxy)-α-methoxymethylbenzylidene]amino]oxy]acetoxy]acetate, n-propyl 2-[[[[2-nitro-5-(2'-chloro-4'-trifluoromethylphenoxy)-α-methoxymethylbenzylidene]amino]oxy]acetoxy]acetate, methyl 2-[[[[2-nitro-5-(2'-chloro-4'-trifluoromethylphenoxy)-α-methoxymethylbenzylidene]amino]oxy]acetoxy]propionate, ethyl 2-[[[[2-nitro-5-(2'-chloro-4'-trifluoromethylphenoxy)-α-methoxymethylbenzylidene]amino]oxy]acetoxy]propionate, n-propyl 2-[[[[2-nitro-5-(2'-chloro-4'-trifluoromethylphenoxy)-α-methoxymethylbenzylidene]amino]oxy]acetoxy]propionate, 5-(2-chloro-4-trifluoromethylphenoxy)-2-nitro-α-methoxyacetophenone oxime-O-acetamide, 5-(2-chloro-4-trifluoromethylphenoxy)-2-nitro-α-methoxyacetophenone oxime-O-(acetic acid, N-methylamide), 5-(2-chloro-4-trifluoromethylphenoxy)-2-nitro-α-methoxyacetophenone oxime-O-(acetic acid, N-ethylamide), 5-(2-chloro-4-trifluoromethylphenoxy)-2-nitro-α-methoxyacetophenone oxime-O-(acetic acid, N-n-propylamide), 5-(2-chloro-4-trifluoromethylphenoxy)-2-nitro-α-methoxyacetophenone oxime-O-(acetic acid, N,N-dimethylamide), 5-(2-chloro-4-trifluoromethylphenoxy)-2-nitro-α-methoxyacetophenone oxime-O-(acetic acid, N-methyl-N-methoxyamide), 5-(2-chloro-4-trifluoromethylphenoxy)-2-nitro-α-methoxyacetophenone oxime-O-[acetic acid, N-(1,1dimethylpropargyl)amide], 5-(2-chloro-4-trifluoromethylphenoxy)-2-nitro-α-methoxyacetophenone oxime-O-(2-propionic acid), sodium 5-(2-chloro-4-trifluoromethylphenoxy)-2-nitro-α-methoxyacetophenone oxime-O-(2-propionate), potassium 5-(2-chloro-4-trifluoromethylphenoxy)-2-nitro-α-methoxyacetophenone oxime-O-(2-propionate), 5-(2-chloro-4-trifluoromethylphenoxy)-2-nitro-α-methoxyacetophenone oxime-O-(2-propionic acid, methyl ester), 5-(2-chloro-4-trifluoromethylphenoxy)-2-nitro-α-methoxyacetophenone oxime-O-(2-propionic acid, ethyl ester), 5-(2-chloro-4-trifluoromethylphenoxy)-2-nitro-α-methoxyacetophenone oxime-O-(2-propionic acid, n-propyl ester), 5-(2-chloro-4-trifluoromethylphenoxy)-2-nitro-α-methoxyacetophenone oxime-O-(2-propionic acid, allyl ester), 5-(2-chloro-4-trifluoromethylphenoxy)-2-nitro-α-methoxyacetophenone oxime-O-(2-propionic acid, 2-methyl-2-propenyl ester), 5-(2-chloro-4-trifluoromethylphenoxy)-2-nitro-α-methoxyacetophenone oxime-O-(2-propionic acid, propargyl ester), 5-(2-chloro-4-trifluoromethylphenoxy)-2-nitro-α-methoxyacetophenone oxime-O-(2-propionic acid, 2chloroethyl ester), 5-(2-chloro-4-trifluoromethylphenoxy)-2-nitro-α-methoxyacetophenone oxime-O-(2-propionic acid, 2methoxyethyl ester), methyl 2-[2-[[[2-nitro-5-(2'-chloro-4'-trifluoromethylphenoxy)-α-methoxymethylbenzylidene]amino]oxy]propionyloxy]acetate, ethyl 2-[2-[[[2-nitro-5-(2'-chloro-4'-trifluoromethylphenoxy)-α-methoxymethylbenzylidene]amino]oxy]propionyloxy]acetate, methyl 2-[2-[[[2-nitro-5-(2'-chloro-4'-trifluoromethylphenoxy)-α-methoxymethylbenzylidene]amino]oxy]propionyloxy]propionate, ethyl 2-[2-[[[2-nitro-5-(2'-chloro-4'-trifluoromethylphenoxy)-α-methoxymethylbenzylidene]amino]oxy]propionyloxy]propionate, 5-(2-chloro-4-trifluoromethylphenoxy)-2-nitro-α-methoxyacetophenone oxime-O-(2-propionamide), 5-(2-chloro-4-trifluoromethylphenoxy)-2-nitro-α-methoxyacetophenone oxime-O-(2-propionic acid, N-methylamide), 5-(2-chloro-4-trifluoromethylphenoxy)-2-nitro-α-methoxyacetophenone oxime-O-(2-propionic acid, N,N-dimethylamide), 5-(2-chloro-4-trifluoromethylphenoxy)-2-nitro-α-methoxyacetophenone oxime-O-(2-propionic acid, N-methyl-N-methoxyamide), 5-(2-chloro-4-trifluoromethylphenoxy)-2-nitro-α-methoxyacetophenone oxime-O-(thioacetic acid, S-methyl ester), 5-(2-chloro-4-trifluoromethylphenoxy)-2-nitro-α-methoxyacetophenone oxime-O-(thioacetic acid, S-ethyl ester), 5-(2-chloro-4-trifluoromethylphenoxy)-2-nitro-α-methoxyacetophenone oxime-O-(thioacetic acid, S-allyl ester), 5-(2-chloro-4-trifluoromethylphenoxy)-2-nitro-α-methoxyacetophenone oxime-O-(2-thiopropionic acid), 5-(2-chloro-4-trifluoromethylphenoxy)-2-nitro-α-methoxyacetophenone oxime-O-(2-thiopropionic acid, Smethyl ester), 5-(2-chloro-4-trifluoromethylphenoxy)-2-nitro-α-methoxyacetophenone oxime-O-(2-thiopropionic acid, S-ethyl ester), methyl 2-[[[[2-nitro-5-(2'-chloro-4'-trifluoromethylphenoxy)-α-methoxymethylbenzylidene]amino]oxy]acetylthio]acetate, ethyl 2-[[[[2-nitro-5-(2'-chloro-4'-trifluoromethylphenoxy)-α-methoxymethylbenzylidene]amino]oxy]acetylthio]acetate, methyl 2-[[[[2-nitro-5-(2'-chloro-4'-trifluoromethylphenoxy)-α-methoxymethylbenzylidene]amino]oxy]acetylthio]propionate, ethyl 2-[[[[2-nitro-5-(2'-chloro-4'-trifluoromethylphenoxy)-α-methoxymethylbenzylidene]amino]oxy]acetylthio]propionate, methyl 2-[2-[[[2-nitro-5-(2'-chloro-4'-trifluoromethylphenoxy)-α-methoxymethylbenzylidene]amino]oxy]propionylthio]acetate, ethyl 2-[2-[[[2-nitro-5-(2'-chloro-4'-trifluoromethylphenoxy)-α-methoxymethylbenzylidene]amino]oxy]propionylthio]acetate,
methyl 2-[2-[[[2-nitro-5-(2'-chloro-4'-trifluoromethylphenoxy)-α-methoxymethylbenzylidene]amino]oxy]propionylthio]propionate, and
ethyl 2-[2-[[[2-nitro-5-(2'-chloro-4'-trifluoromethylphenoxy)-α -methoxymethylbenzylidene]aminoloxy]propionylthio]propionate.

The compounds represented by the above-mentioned formula (I) in which Y is an oxygen atom include:
5-(2-chloro-4-trifluoromethylphenoxy)-2-nitro-α-methoxyacetophenone,
2-nitro-5-(2-chloro-4-trifluoromethylphenoxy)-phenacyloxyacetic acid,
methyl 2-nitro-5-(2-chloro-4-trifluoromethylphenoxy)-phenacyloxyacetate,
ethyl 2-nitro-5-(2-chloro-4-trifluoromethylphenoxy)-phenacyloxyacetate,
n-propyl 2-nitro-5-(2-chloro-4-trifluoromethylphenoxy)phenacyloxyacetate,
n-butyl 2-nitro-5-(2-chloro-4-trifluoromethylphenoxy)-phenacyloxyacetate,
allyl 2-nitro-5-(2-chloro-4-trifluoromethylphenoxy)-phenacyloxyacetate,
propargyl 2-nitro-5-(2-chloro-4-trifluoromethylphenoxy)phenacyloxyacetate,
2-chloroethyl 2-nitro-5-(2-chloro-4-trifluoromethylphenoxy)phenacyloxyacetate,
2-methoxyethyl 2-nitro-5-(2-chloro-4-trifluoromethylphenoxy)phenacyloxyacetate,
1-methyl-2-methoxyethyl 2-nitro-5-(2-chloro-4-trifluoromethylphenoxy)phenacyloxyacetate,
methyl 2-[2-nitro-5-(2'-chloro-4'-trifluoromethylphenoxy)phenacyloxyacetoxy]acetate,
ethyl 2-[2-nitro-5-(2'-chloro-4'-trifluoromethylphenoxy)phenacyloxyacetoxy]acetate,
methyl 2-[2-nitro-5-(2'-chloro-4'-trifluoromethylphenoxy)phenacyloxyacetoxy]propionate,
ethyl 2-[2-nitro-5-(2'-chloro-4'-trifluoromethylphenoxy)phenacyloxyacetoxy]propionate,
2-[2-nitro-5-(2'-chloro-4'-trifluoromethylphenoxy)-phenacyloxy]propionic acid,
methyl 2-[2-nitro-5-(2'-chloro-4'-trifluoromethylphenoxy)phenacyloxy]propionate,
ethyl 2-[2-nitro-5-(2'-chloro-4'-trifluoromethylphenoxy)phenacyloxy]propionate,
n-propyl 2-[2-nitro-5-(2'-chloro-4'-trifluoromethylphenoxy)phenacyloxy]propionate,
isopropyl 2-[2-nitro-5-(2'-chloro-4'-trifluoromethylphenoxy)phenacyloxy]propionate,
n-butyl 2-[2-nitro-5-(2'-chloro-4'-trifluoromethylphenoxy)phenacyloxy]propionate,
allyl 2-[2-nitro-5-(2'-chloro-4'-trifluoromethylphenoxy)phenacyloxy]propionate,
propargyl 2-[2-nitro-5-(2'-chloro-4'-trifluoromethylphenoxy)phenacyloxy] propionate,
2-chloroethyl 2-[2-nitro-5-(2'-chloro-4'trifluoromethylphenoxy)phenacyloxy]propionate,
2-methoxyethyl 2-[2-nitro-5-(2'-chloro-4'trifluoromethylphenoxy)phenacyloxy]propionate,
methyl 2-[2-[2'-nitro-5'-(2''-chloro-4''-trifluoromethylphenoxy)phenacyloxy]propionyloxy]acetate,
ethyl 2-[2-[2'-nitro-5'-(2''-chloro-4''-trifluoromethylphenoxy)phenacyloxy]propionyloxy]acetate,
methyl 2-[2-[2'-nitro-5'-(2''-chloro-4''-trifluoromethylphenoxy)phenacyloxy]propionyloxy]propionate,
ethyl 2-[2-[2'-nitro-5'-(2''-chloro-4''-trifluoromethylphenoxy)phenacyloxy]propionyloxy]propionate,
S-methyl 2-[2-nitro-5-(2'-chloro-4'-trifluoromethylphenoxy)phenacyloxy]thioacetate,
S-ethyl 2-[2-nitro-5-(2'-chloro-4'-trifluoromethylphenoxy)phenacyloxy]thioacetate,
S-allyl 2-[2-nitro-5-(2'-chloro-4'-trifluoromethylphenoxy)phenacyloxy]thioacetate,
S-propargyl 2-[2-nitro-5-(2'-chloro-4'-trifluoromethylphenoxy)phenacyloxy]thioacetate,
methyl 2-[2-nitro-5-(2'-chloro-4'-trifluoromethylphenoxy)phenacyloxyacetylthio]acetate,
ethyl 2-[2-nitro-5-(2'-chloro-4'-trifluoromethylphenoxy)phenacyloxyacetylthio]acetate,
methyl 2-[2-nitro-5-(2'-chloro-4'-trifluoromethylphenoxy)phenacyloxyacetylthio]propionate,
ethyl 2-[2-nitro-5-(2'-chloro-4'-trifluoromethylphenoxy)phenacyloxyacetylthio]propionate,
S-methyl 2-[2-nitro-5-(2'-chloro-4'-trifluoromethylphenoxy)phenacyloxy]thiopropionate,
S-ethyl 2-[2-nitro-5-(2'-chloro-4'-trifluoromethylphenoxy)phenacyloxy]thiopropionate,
S-allyl 2-[2-nitro-5-(2'-chloro-4'-trifluoromethylphenoxy)phenacyloxy]thiopropionate,
S-propargyl 2-[2-nitro-5-(2'-chloro-4'-trifluoromethylphenoxy)phenacyloxy]thiopropionate,
methyl 2-[2-[2'-nitro-5'-(2''-chloro-4''-trifluoromethylphenoxy)phenacyloxy]propionylthio]acetate,
ethyl 2-[2-[2'-nitro-5'-(2''-chloro-4''-trifluoromethylphenoxy)phenacyloxy]propionylthio]acetate,
methyl 2-[2-[2'-nitro-5'-(2''-chloro-4''-trifluoromethylphenoxy)phenacyloxy]propionylthio]propionate, and
ethyl 2-[2-[2'-nitro-5'-(2''-chloro-4''-trifluoromethylphenoxy)phenacyloxy]propionylthio]propionate.

All of the above compounds are novel compounds which have not been disclosed in any literature. They may be prepared according to, for example, Method A to Method D as described below.

In another aspect of the present invention, there is provided a compound represented by the formula

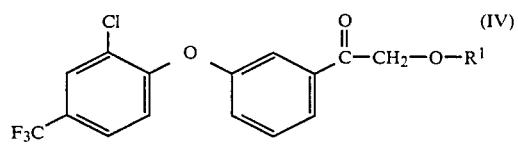

wherein R¹ is as defined above.

In a further aspect of the present invention, there is provided a compound represented by the formula

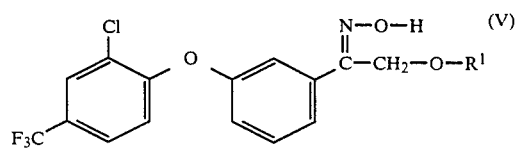

wherein R¹ is as defined above.

In still a further aspect of the present invention, there is provided a compound represented by the formula

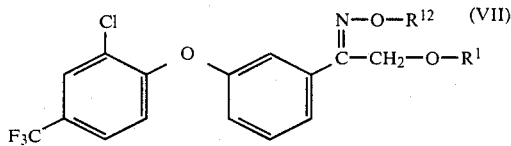 (VII)

All of the compounds (IV), (V) and (VII) are novel compounds which are useful as intermediates for the novel compound represented by the formula (I). wherein $R^1$ is defined above and $R^{12}$ represents an alkyl group having 1 to 3 carbon atoms or

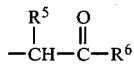

in which
  $R^5$ represents a hydrogen atom or a methyl group, and
  $R^6$ represents —$BR^7$ or

in which
  B represents an oxygen atom or a sulfur atom, $R^7$ represents a hydrogen atom, and alkyl group having 1 to 4 carbon atoms, an alkenyl group having 3 to 6 carbon atoms, an alkynyl group having 3 to 6 carbon atoms, a substituted or unsubstituted phenyl group, an alkyl group having 1 to 4 carbon atoms and substituted with a halogen atom or an alkoxy group having 1 to 3 carbon atoms, an alkali metal, an alkaline earth metal in proportion corresponding to mono-valency of the alkaline earth metal, an ammonium group, an ammonium group substituted with an alkyl group having 1 to 4 carbon atoms, or

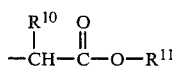

in which
  $R^{10}$ represents a hydrogen atom or a methyl group, and
  $R^{11}$ represents an alkyl group having 1 to 3 carbon atoms, and
  $R^8$ and $R^9$ are identical or different and each independently represent a hydrogen atom, an alkyl group having 1 to 3 carbon atoms, an alkynyl group having 3 to 6 carbon atoms, or an alkoxy group having 1 to 3 carbon atoms. Those compounds (IV), (V) and (VII) may be prepared according to, for example, methods as described in Method A given below.

In an additional aspect of the present invention, there is provided a process for preparing a compound represented by the formula

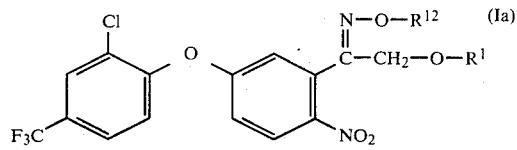 (Ia)

wherein $R^1$ and $R^{12}$ are as defined above, which comprises: reacting a compound represented by the formula

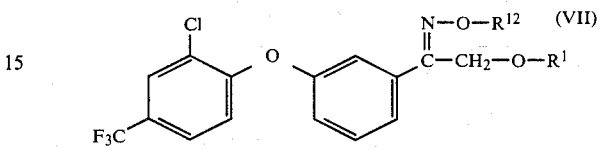 (VII)

in which $R^1$ and $R^{12}$ are as defined above, with a nitrating agent.

In an even further aspect of the present invention, there is provided a process for preparing a compound represented by the formula

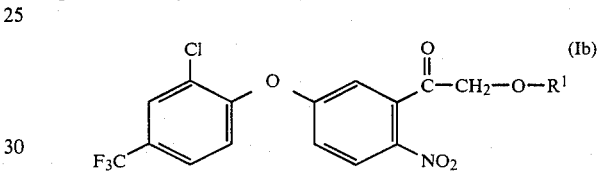 (Ib)

wherein $R^1$ is as defined above, which comprises: reacting a compound represented by the formula

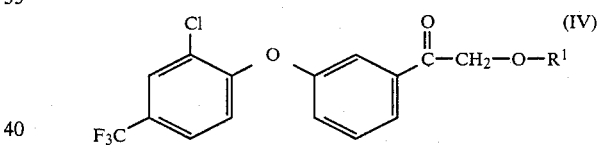 (IV)

in which $R^1$ is as defined above, with a nitrating agent.

In an even further aspect of the present invention, there is provided a process for preparing a compound represented by the formula

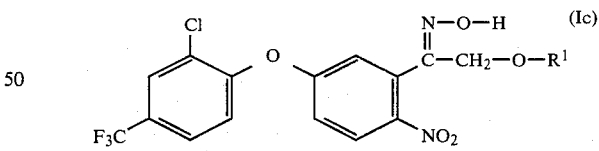 (Ic)

wherein $R^1$ is as defined above, which comprises: reacting a compound represented by the formula

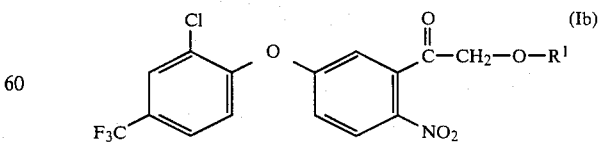 (Ib)

in which $R^1$ is as defined above, with hydroxylamine hydrochloride in the presence of an acid acceptor.

In an even further aspect of the present invention, there is provided a process for preparing a compound represented by the formula

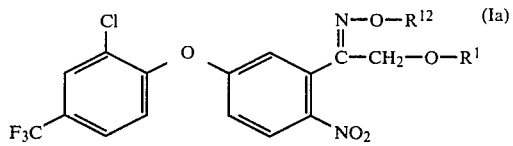

wherein $R^1$ and $R^{12}$ are as defined above, which comprises: reacting a compound represented by the formula

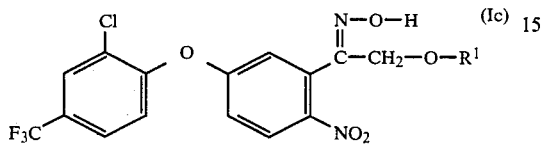

in which $R^1$ is as defined above, with a halide represented by the formula $$R^{12}\text{-}Z \qquad (VI)$$

in which $R^{12}$ is as defined above, and Z represents a halogen atom, in the presence of an acid acceptor.

As examples of the above-mentioned process, there will be illustratively mentioned Methods A to D below.

Method A
Reaction process:

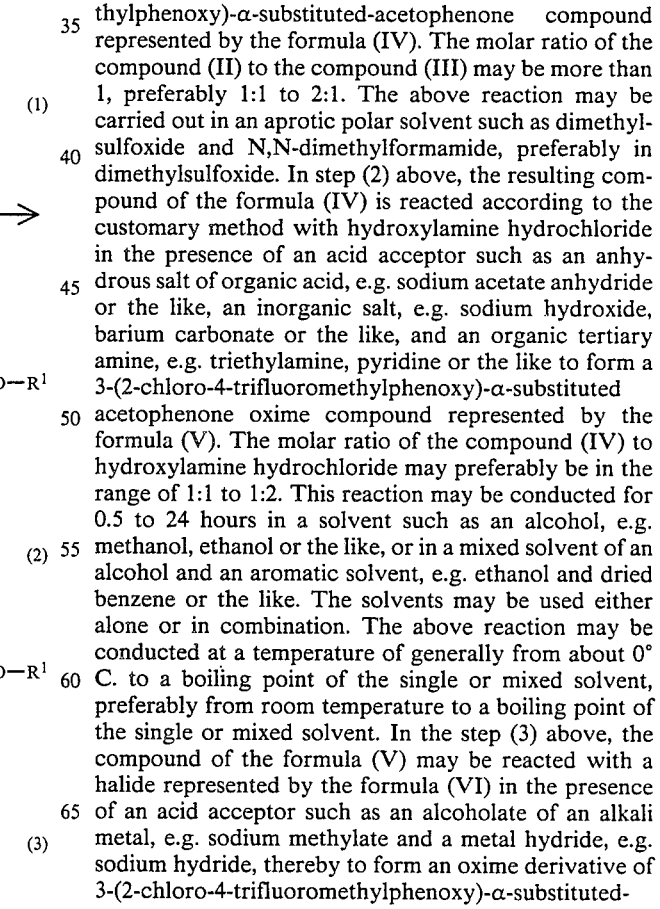

wherein M represents an alkali metal, Z represents a halogen atom, and $R^1$ and $R^{12}$ are as defined hereinbefore.

In step (1) above, a 3-chloro-4-halogenobenzotrifluoride compound represented by the formula (II) is reacted with a sodium or potassium salt, preferably a potassium salt of a 3-hydroxy-α-substituted-acetophenone compound represented by the formula (III) or ketal or acetal derivative thereof at a temperature of from 70° to 160° C., preferably from 90° to 140° C. for about 1 to 8 hours to form a 3-(2-chloro-4-trifluoromethylphenoxy)-α-substituted-acetophenone compound represented by the formula (IV). The molar ratio of the compound (II) to the compound (III) may be more than 1, preferably 1:1 to 2:1. The above reaction may be carried out in an aprotic polar solvent such as dimethylsulfoxide and N,N-dimethylformamide, preferably in dimethylsulfoxide. In step (2) above, the resulting compound of the formula (IV) is reacted according to the customary method with hydroxylamine hydrochloride in the presence of an acid acceptor such as an anhydrous salt of organic acid, e.g. sodium acetate anhydride or the like, an inorganic salt, e.g. sodium hydroxide, barium carbonate or the like, and an organic tertiary amine, e.g. triethylamine, pyridine or the like to form a 3-(2-chloro-4-trifluoromethylphenoxy)-α-substituted acetophenone oxime compound represented by the formula (V). The molar ratio of the compound (IV) to hydroxylamine hydrochloride may preferably be in the range of 1:1 to 1:2. This reaction may be conducted for 0.5 to 24 hours in a solvent such as an alcohol, e.g. methanol, ethanol or the like, or in a mixed solvent of an alcohol and an aromatic solvent, e.g. ethanol and dried benzene or the like. The solvents may be used either alone or in combination. The above reaction may be conducted at a temperature of generally from about 0° C. to a boiling point of the single or mixed solvent, preferably from room temperature to a boiling point of the single or mixed solvent. In the step (3) above, the compound of the formula (V) may be reacted with a halide represented by the formula (VI) in the presence of an acid acceptor such as an alcoholate of an alkali metal, e.g. sodium methylate and a metal hydride, e.g. sodium hydride, thereby to form an oxime derivative of 3-(2-chloro-4-trifluoromethylphenoxy)-α-substitutedacetophenone represented by the formula (VII). The molar ratio of the compound (V) to the compound (VI) may preferably be in the range of from 1:1 to 1:2. This reaction may be conducted in a suitable solvent selected from an alkanol solvent such as methanol and ethanol, an ether solvent such as diethyl ether and tetrahydrofuran, an aprotic polar solvent such as N,N-dimethylformamide and N,N-dimethylacetamide, and an aromatic solvent such as benzene. The solvents may be used either alone or in combination. This reaction may be conducted at a temperature of generally from about −10° to about 150° C., preferably from about 0° to about 100° C. In step (4) above, the compound of the formula (VII) is reacted with a customary nitrating agent such as potassium nitrate in concentrated sulfuric acid, a mixed acid of sulfuric acid and nitric acid, and the like to obtain a compound represented by the formula (Ia) according to the present invention. The molar ratio of the compound (VII) to a nitrating agent may preferably be in the range of from 1:1 to 1:1.5. The nitration may be conducted at a temperature of generally from about −20° C. to about 80° C., preferably from about −10° C. to about 50° C. for about 0.5 to 6 hours. According to need, the nitration may be conducted in an inert organic solvent such as 1,2-dichloroethane and other chlorohydrocarbons.

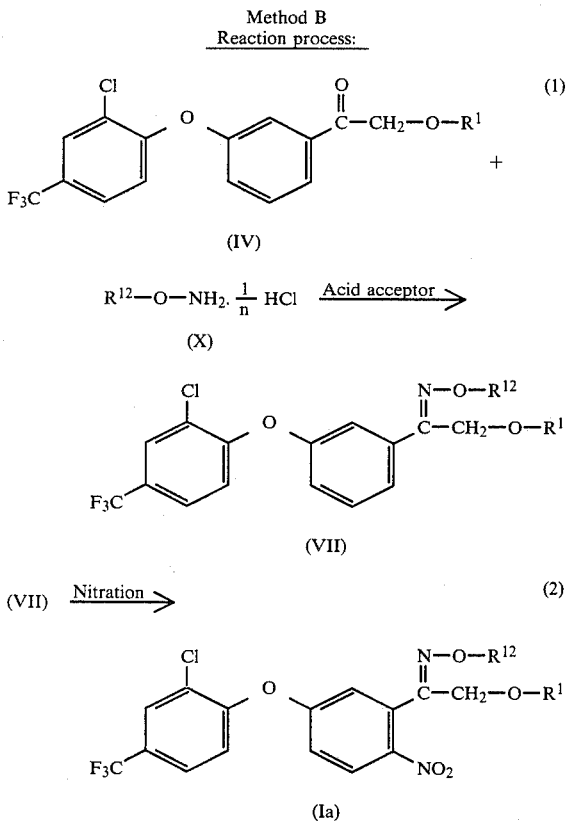

wherein $R^1$ and $R^{12}$ are as defined above, and n is an integer of 1 or 2.

In step (1) above, according to a customary method, a 3-(2-chloro-4-trifluoromethylphenoxy)-α-substituted-acetophenone compound represented by the formula (IV) may be reacted with a hydrochloride of a hydroxylamine derivative represented by the formula (X) in the presence of an acid acceptor such as an anhydrous salt of an organic acid, e.g. sodium acetate anhydride, an inorganic salt, e.g. sodium hydroxide and barium carbonate, and an organic tertiary amine, e.g. triethylamine and pyridine to form an oxime derivative of 3-(2-chloro-4-trifluoromethylphenoxy)-α-substituted-acetophenone represented by the formula (VII). The molar ratio of the compound (IV) to the compound (X) is preferably in the range of from 1:1 to 1:2. This reaction may be performed in an organic solvent such as an alcohol, e.g. anhydrous ethanol, and a mixed solvent of an alcohol and aromatic solvent, e.g. anhydrous ethanol and dried benzene. The solvents may be used either alone or in combination. The reaction may be conducted at the same temperature as that described in step (2) of Method A for about 0.5 to 24 hours.

In step (2) above, the nitration reaction is effected in substantially the same manner as described in step (4) of Method A, thereby to obtain a compound of the formula (Ia) according to the present invention.

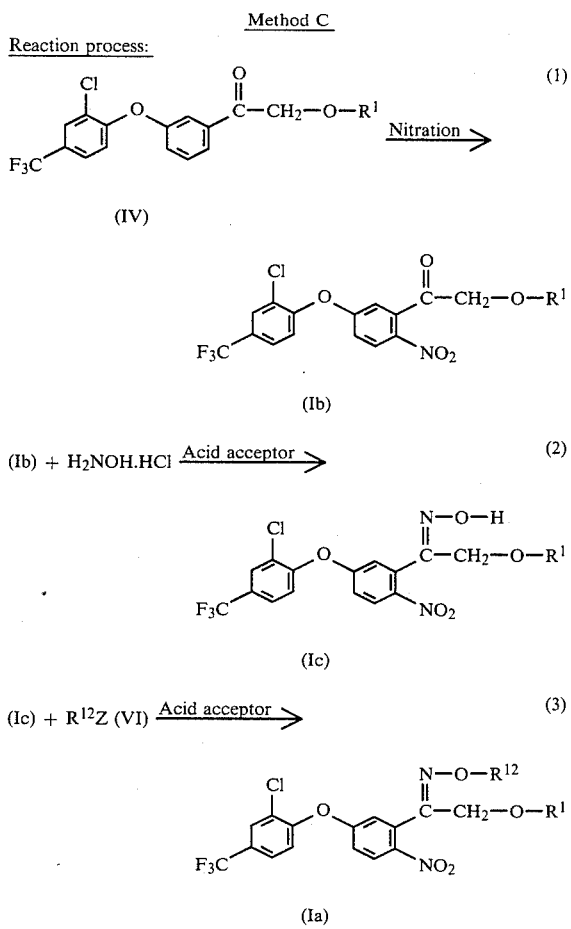

wherein $R^1$, $R^{12}$ and Z are as defined hereinbefore.

In step (1) above, a 3-(2-chloro-4-trifluoromethylphenoxy)-α-substituted-acetophenone compound represented by the formula (IV) is nitrated in substantially the same manner as described in step (4) of Method A to obtain a compound of the formula (Ib) according to the present invention.

Then, in step (2) above, the obtained compound of the formula (Ib) is reacted with hydroxylamine hydrochloride in the presence of an acid acceptor to form an oxime represented by the formula (Ic) according to the present invention. This reaction may be conducted in substantially the same manner as described in step (2) of Method A except that the molar ratio of the compound (Ib) to hydroxylamine hydrochloride may preferably be in the range of 1:1 to 1:5.

Further, in step (3) above, the obtained oxime of the formula (Ic) is reacted with a halide represented by the formula (VI) in the presence of an acid acceptor in substantially the same manner as described in step (3) of Method A to obtain a compound represented by the formula (Ia) according to the present invention.

Method D
Reaction process

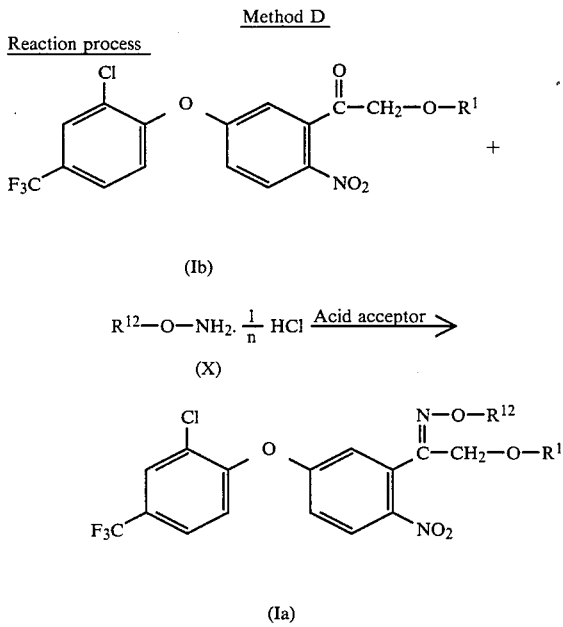

(Ib)

(Ia)

wherein $R^1$, $R^{12}$ and n are as defined above.

In this method, an α-substitued-acetophenone derivative represented by the formula (Ib) is reacted with a hydrochloride of a hydroxylamine derivative represented by the formula (X) to obtain a compound represented by the formula (Ia) according to the present invention. This reaction is conducted in the presence of an acid acceptor such as an anhydrous slat of an organic acid, e.g. sodium acetate anhydride, an inorganic salt, e.g. sodium hydroxide and barium carbonate, and an organic tertiary amine, e.g. triethylamine and pyridine. A preferred molar ratio of the compound (Ib) to the compound (X) may be 1:1 to 1:5, and the reaction time may be 0.5 to 24 hours. This reaction may be performed in an organic solvent such as an alcohol, e.g. anhydrous ethanol, and a mixed solvent of an alcohol and aromatic solvent, e.g. anhydrous ethanol and dried benzene. The solvents may be used either alone or in combination. This reaction may be conducted at a temperature as described in step (2) of Method A.

The above Methods A to D are illustrative of preferred processes of the present invention. It should be understood that these methods are not intended to limit the present invention. The compounds of the present invention may be produced by various methods which are modifications of conventionally known methods for producing similar compounds.

In an even further aspect of the present invention, there is provided a herbicidal composition which comprises as an active ingredient a herbicidally effective amount of a compound represented by the formula

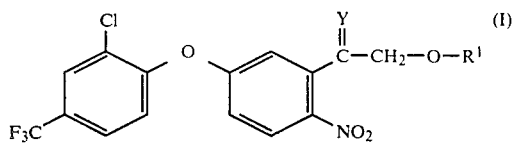

wherein $R^1$ and Y are as defined above.

The term "a herbicidally effective amount" used herein is intended to mean an amount required under the environmental conditions in order to effectively control, that is, the weeds are severely injured so as not to be able to recover from the application of the compound or are killed, and no substantial injury is caused to the crops.

The herbicidal activity of the compound (I) of the present invention is illustrated hereinbelow with respect to the prevention and elimination of the weeds which grow on plowed fields. The compound (I) of the present invention can be effectively applied to plowed fields in a prolonged period, in both of the preemergence and postemergence applications, and exhibits extremely high herbicidal activity even at a surprisingly low dosage thereof. The compound (I) of the present invention exhibits excellent herbicidal activity to hazardous weeds growing on plowed fields such as weeds belonging to family Granmineae, e.g. crabgrass, green foxtail, barnyardgrass and the like; broad-leaved weeds, e.g. lambsquarter, smartweed, velvetleaf, cocklebur, hemp sesbania, livid amaranth, morningglory, teaweed, sicklepod, jimsonweed, black nightshade, bindweed, common chickweed, common purslane and the like; and other various weeds. Of them, especially, velvetleaf, cocklebur, jimsonweed, morningglory, hemp sesbania and teaweed, all of which are hazardous weeds in soybean fields, are effectively controlled by the compound (I) of the present invention at a surprisingly low dosage.

Thus, the characteristic feature of the compound (I) of the present invention resides in that the compound exhibits, in both of the preemergence and postemergence applications, an excellent herbicidal activity and also excellent selectivity for not only broad-leaved crop plants such as soybean, peanut plants and the like but also crop plants belonging to the family Gramineae such as corn, wheat, rice plants and the like.

Further, the compound of the present invention exhibits extremely high herbicidal activities not only to the plowed field weeds but also to the paddy field weeds.

That is, the compound (I) of the present invention exhibits high herbicidal activities, even in a small dosage, to a variety of weeds on paddy fields, for example, the hazardous weeds belonging to the family Gramineae such as barnyardgrass and the like; broad-leaved weeds growing on paddy fields such as monochoria, toothcup, waterwort, false pimpernel and the like; perennial weeds on paddy fields such as arrowhead, flat sedge and the like. The compound (I) of the present invention has no significant phytotoxicity to rice plants when it is applied in such a herbicidally effective amount that the weeds are destroyed effectively.

As is apparent from the foregoing, the compound (I) of the present invention can be utilized for selective destruction of weeds growing among plants of soybean, peanut, corn, wheat, barley, rice and the like, in both the preemergence and postemergence applications. Further, due to its wide applicability and excellent herbicidal activities, the compound (I) of the present invention is also useful as an effective herbicide for a pasture, an orchard, a lawn and a noncropland.

In practical application of the present compound as a herbicide, it may be applied as such, or may be formulated into various types of preparations, such as wettable powder, emulsifiable concentrate, granule, dust and the like.

As the solid carrier to be used for formulating the present compound into the above-described various preparations, there may be mentioned mineral powder (e.g. kaolin, bentonite, clay, montmorillonite, talc, diatomite, mica, vermiculite, gypsum, calcium carbonate, apatite and the like), vegetable powder (e.g. soybean meal, wheat flour, wood meal, tobacco powder, starch, crystalline cellulose and the like), high polymer compounds (e.g. petroleum resin, polyvinyl chloride, ketone resin and the like) and, further, alumina and waxes. As the liquid carrier, there may be mentioned, for example, alcohols (methanol, ethanol, butanol, ethylene glycol, benzyl alcohol and the like), aromatic hydrocarbons (such as toluene, benzene, xylene and the like), chlorinated hydrocarbons (chloroform, carbon tetrachloride, monochlorobenzene and the like), ethers (dioxane, tetrahydrofuran and the like), ketones (acetone, methyl ethyl ketone, cyclohexanone and the like), esters (ethyl acetate, butyl acetate and the like), acid amids (N,N-dimethylacetamide and the like), nitriles (acetonitrile and the like), ether alcohols (ethylene glycol ethyl ether and the like) and water.

As the surface active agent to be used to effect emulsifying, dispersing, spreading and the like for the present compound (I), there may be mentioned nonionic, anionic, cationic and amphoteric ones. Specific examples of the surface active agent which can be employed in the present invention are a polyoxyethylene alkyl ether, a polyoxyethylene alkylaryl ether, a polyoxyethylene fatty acid ester, a sorbitan fatty acid ester, a polyoxyethylene sorbitan fatty acid ester, an oxyethylene polymer, an oxypropylene polymer, a polyoxyethylene alkyl phosphate, a fatty acid salt, an alkyl sulfate salt, an alkyl sulfonate salt, an alkyl aryl sulfonate salt, an alkyl phosphate salt, a polyoxyethylene alkyl sulfate, a quaternary ammonium salt and an oxyalkylamine. Further, according to need, gelatin, casein, sodium alginate, starch, agar, polyvinyl alcohol and the like may be used as an auxiliary additive in the present invention.

The content of the compound (I) of the present invention in the herbicidal composition may vary depending on the type of the composition and the purpose for which the composition is designed, however, be generally from about 0.05 to 95% by weight, preferably about 5 to 75% by weight based on the total weight of the composition.

Moreover, in order to improve the effect as a herbicide, the compound (I) of the present invention may be mixed with other herbicidally active ingredients and, in some cases, a synergistic effect is expectable. For example, the following ingredients may be mixed with the compound (I) of the present invention.

(A) Phenoxy type herbicide 2,4-dichlorophenoxyacetic acid; 2-methyl-4-chlorophenoxyacetic acid; butyl 2-[4-(5-trifluoromethyl-2-pyridyloxy)phenoxy]propionate (including esters and salts thereof); ethyl 2-[4-(6-chloro-2-quinoxalinyloxy)-phenoxy]propionate; etc.

(B) Diphenyl ether type herbicide 2,4,6-trichlorophenyl 4'-nitrophenyl ether; 2,4-dichlorophenyl 4'-nitro-3'-methoxyphenyl ether; 2,4-dichlorophenyl 3'-methoxycarbonyl-4'-nitrophenyl ether; 2-chloro-4-trifluoromethylphenyl 3'-ethoxy-4'-nitrophenyl ether; sodium 5-[2-chloro-4-(trifluoromethyl)phenoxy]-2-nitrobenzoate; 5-(2-chloro-4-trifluoromethylphenoxy)-N-methylsulfonyl-2-nitrobenzamide; ethyl 2-[2-nitro-5-(2'-chloro-4'-trifluoromethylphenoxy)benzoyloxy] propionate; 5-(2-chloro-4-trifluoromethylphenoxy)-2-nitroacetophenone oxime-O-(acetic acid, methyl ester); etc.

(C) Triazine type herbicide 2-chloro-4,6-bis-ethylamino-1,3,5-triazine; 2-choloro-4-ethylamino-6-isopropylamino-1,3,5-triazine; 2-methylthio-4,6-bis-ethylamino-1,3,5,-triazine; 4-amino-6-tert-butyl-3-methylthio-1,2,4-triazine-5(4H)-one; etc.

(D) Urea type herbicide 3-(3,4-dichlorophenyl)-1,1-dimethylurea; 3-(3,4-dichlorophenyl)-1-methoxy-1-methylurea; 3-(α,α,α-trifluoro-m-tolyl)-1,1-dimethylurea; 3-[4-(4-methylphenethyloxy)phenyl]-1-methoxy-1-methylurea; 3-(5-t-butyl-3,4-thiadiazol-2-yl)-4-hydroxy-1-methyl-2-imidazolidone; etc.

(E) Carbamate type herbicide isopropyl N-(3-chlorophenyl)carbamate; methyl N-(3,4-dichlorophenyl)carbamate; 4-chloro-2-butynyl N-(3-chlorophenyl)carbamate; etc.

(F) Thiolcarbamate type herbicide

S-ethyl N,N-hexamethylenethiolcarbamate; S-(4-chlorobenzyl) N,N-diethylthiolcarbamate; S-ethyl dipropylthiolcarbamate; etc.

(G) Anilide type herbicide

3',4'- -dichloropropionanilide; N-methoxymethyl-2',6'-diethyl-2-chloroacetanilide; 2-chloro-2',6'-diethyl-N-(butoxymethyl)acetanilide; 2-chloro-2',6'-diethyl-N-(propoxyethyl)acetanilide; α-(2-naphthoxy)propionanilide; etc.

(H) Uracil type herbicide 5-bromo-3-sec-butyl-6-methyluracil; 3-cyclohexyl-5,6-trimethyleneuracil; etc.

(I) Dipyridinium salt type herbicide 1,1'-dimethyl-4,4'-dipyridinium dichloride; 1,1'-ethylene-2,2'-dipyridinium dibromide; etc.

(J) Phosphorus type herbicide

N-(phosphonomethyl)glycine; O-ethyl,O-(2-nitro-5-methylphenyl) N-sec-butylphosphoroamidothioate; O-methyl,O-(2-nitro-4-methylphenyl) N-isopropylphosphoroamidothioate; S-(2-methyl-1,1'-piperidylcarbonylmethyl)-O,O-di-n-propyl dithiophosphate; (2-amino-4-methylphosphinobutyryl)alanylalanine monosodium salt; etc.

(K) Toluidine type herbicide

α,α,α-trifluoro-2,6-dinitro-N,N-dipropyl-p-toluidine; N-(cyclopropylmethyl)-α,α,α-trifluoro-2,6-dinitro-N-propyl-p-toluidine; etc.

(L) Other herbicides 5-t-butyl-3-(2,4-dichloro-5-isopropoxyphenyl)-1,3,4-oxadiazolin-2-one; 3-isopropyl-1H-2,1,3-benzothiazidine-4(3H)-one 2,2-dioxide; 2-(α-naphthoxy)-N,N-diethylpropionamide; 3-amino-2,5-dichlorobenzoic acid; 4-(2,4-dichlorobenzoyl)-1,3-dimethylpyrazol-5-yl-p-toluene sulfonate; 2-chloro-N-[(4-methoxy-6-methyl-1,3,5-triazine-2-yl)aminocarbonyl]benzenesulfonamide; methyl 2-[(4,6-dimethoxypyrimidin-2-yl)aminocarbonylaminosulfonylmethyl]benzoate; N-(1-methyl-1-phenylethyl)-2-bromo3,3-dimethylbutanamide; 2-[1-(N-allyloxyamino)butylidene]-4-methoxycarbonyl-5,5-dimethylcyclohexane-1,3-dione sodium salt; 2-[1-

(ethoxyimino)butyl]-5-(2-ethylthiopropyl)-3-hydroxy-2-cyclohexen-1-one; exo-1-methyl-4-(1-methylethyl)-2-[(2-methylphenyl)methoxy]-7-oxabicyclo[2,2,1]heptane; ethyl 2-[[[[4-chloro-6-methoxypyrimidin-2-yl]amino]carbonyl]amino]sulfonyl]benzoate; 2-(4-isopropyl-4-methyl-5-oxo-2-imidazolin-2-yl)nicotinic acid; methyl 2-[4,5-dihydro-4-methyl-4-(1-methylethyl)-5-oxo-1H-imidazol-2-yl]-3-quinolinecarboxylate; 2-(2-chlorophenyl)methyl-4,4-dimethyl-3-isoxazolidinone; etc.

The foregoing herbicides are mentioned only as the examples, and they should not be construed to be limiting the scope of herbicides which can be utilized in combination with the compound (I) of the present invention. The herbicide of the present invention may also be applied in combination with insecticides such as pyrethroid type insecticides, fungicides, plant growth regulators, microbial agricultural chemicals and fertilizers.

The above-mentioned other ingredients may be mixed with the compound (I) of the present invention, to prepare a herbicidal composition, in an amount of about 5 to 95% by weight, based on the total weight of the active ingredients in the herbicidal composition.

In an even further aspect of the present invention, there is provided a method for the destruction of undesirable weeds, which comprises applying to said weeds a herbicidally effective amount of a compound represented by the formula

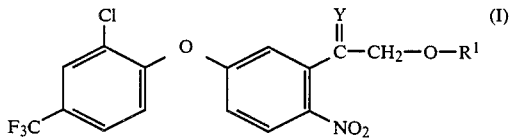

wherein Y and $R^1$ are as defined above, as such or in the form of a herbicidal composition comprising said compound (I) as an active ingredient and an agriculturally acceptable carrier as defined above. The term "applying to the weeds" as used herein means any method of contacting the weeds, both preemergence (before the weeds appear) and/or post-emergence (after the weeds appear), such as applying granules of the compound to the soil prior to emergence, or spraying a solution of the compound or compounds described by the formula (I), or any other method known in the art by which the weeds are contacted either before they emerge or after they emerge, or both before and after they emerge, but preferably after they emerge with one or more of the compounds represented by the formula (I) described herein. The dosage of the compounds (I) according to the present invention may be in the range of from 0.5 to 150 g/10 a, preferably from 1 to 70 g/10 a. The above-described method is useful in effectively and selectively controlling undesirable weeds at a lower dosage of the compounds of the present invention than those of the conventional diphenyl ether type herbicids. The selective herbicidal activity is especially high when the compounds (I) of the present invention is applied to undesirable weeds among soybean plants. Further, the above-described method is continuously useful through the whole period of growth of crop plants including broadleaved crop plants such as soybean, and peanut, and crop plants belonging to the family Gramineae such as coan, wheat, barley and rice plants.

In Application Examples which will be given later and in which the active compound is applied in the form of a herbicidal composition, the dosage of the composition is expressed using the unit "a.i. g/10 a" which means "g/10 a in terms of the amount of an active ingredient".

EXAMPLE

The present invention will now be explained in more detail with reference to Examples with respect to the preparation of the compounds of the present invention and Application Examples with respect to the recipes and effectiveness of the compounds of the present invention as a herbicide. These Examples are not to be construed as limiting the scope of the present invention in any manner.

EXAMPLE 1

Preparation of 5-(2-chloro-4-trifluoromethylphenoxy)-2-nitro-α-methoxyacetophenone: Compound No. 51

(a) 63 g of 3-chloro-4-fluorobenzotrifluoride and 61 g of 3'-hydroxy-2-methoxyacetophenone potassium salt were added to 200 ml of dimethylsulfoxide. Then, the reaction was effected at 100° C. for 3 hours. After completion of the reaction, the liquid reaction mixture was poured into ice-water, followed by extraction of the reaction product with ether. The ether layer was washed with water an dried over anhydrous sodium sulfate, followed by evaporation-removal of the ether under reduced pressure. The obtained residue was subjected to vacuum distration to obtain a fraction at 160° C. to 170° C. under 2.5 mmHg. The thus obtained fraction was allowed to stand to obtain 85 g of a while crystalline substance of 3-(2-chloro-4-trifluoromethylphenoxy)-α-methoxyacetophenone having a melting point of 104.5° C. to 106° C. The NMR spectral data of this compound were as follows.

$^1$H-NMR spectral data [CDCl$_3$, δ(ppm)]: 3.43 (s, 3H), 4.58 (s, 2H), 6.84–7.70 (m, 7H)

(b) 3.4 g of 3-(2-chloro-4-trifluoromethylphenoxy)-αphenoxy)-α-methoxyacetophenone as obtained in step (a) above was added to a mixture of 20 ml of dichloromethane and 10 ml of concentrated sulfuric acid which mixture had been cooled to below 5 ° C. Subsequently, 1 g of potassium nitrate was gradually added over a period of 10 minutes. After completion of the addition, the reaction was allowed to proceed at below 5° C. for 30 minutes. Then, the reaction mixture was poured into ice-water, followed by addition of 50 ml of dichloromethane. The dichloromethane layer was separated by extraction, washed with an aqueous sodium chloride saturated solution and with water, and dried over anhydrous sodium sulfate, followed by evaporation-removal of the dichloromethane under reduced pressure to obtain a crude product. The thus obtained crude product was subjected to purification by the silica gel column chromatography. As a result, there was obtained 2.3 g of a light brown crystalline substance of 5-(2-chloro-4-trifluoromethylphenoxy)-2-nitro-α-methoxyacetophenone having a melting point of 95° C. to 96° C.

EXAMPLE 2

Preparation of syn- and anti-isomers of 5-(2-chloro-4-trifluoromethylphenoxy)-2-nitro-α-methoxyacetophenone oxime: Compound No. 1 and Compound No. 2

3.9 g of 5-(2-chloro-4-trifluoromethylphenoxy)-2-nitro-α-metoxyacetophenone (Compound No. 51) as prepared in Example 1 was dissolved in a mixture of 20 ml of anhydrous ethanol and 20 ml of dried benzene. To the resulting solution were added 1.4 g of anhydrous sodium acetate and 1.2 g of hydroxylamine hydrochloride. The mixture was heated under reflux for 8 hours and then cooled, followed by extraction of the reaction product by addition of water and ether. The organic layer was washed with water and dried over anhydrous sodium sulfate, followed by evaporation-removal of the ether and benzene under reduced pressure to obtain a reaction product composed of syn- and anti-isomers of 5-(2-chloro-4-trifluoromethylphenoxy)-2-nitro-α-methoxyacetophenone oxime. The thus obtained product was subjected to separation and purification by the silica gel column chromatography. As a result, there were obtained 1.8 g of light brown crystals of syn-isomer of the oxime having a melting point of 123° C. to 125° C. (Compound No. 1) and 1.4 g of a light yellow viscous oily substance of anti-isomer of the oxime having a refractive index $n_D^{30}$ of 1.5278 (Compound No. 2).

EXAMPLE 3

Preparation of syn- and anti-isomers of 5-(2-chloro-4-trifluoromethylphenoxy)-2-nitro-α-methoxyacetophenone oxime-O-(acetic acid, methyl ester): Compound No. 9

(a) 3.4 g of 3-(2-chloro-4-trifluoromethylphenoxy)-α-methoxyacetophenone as prepared in the same manner as in step (a) of Example 1 was dissolved in 20 ml of ethanol, followed by addition of 1 g of anhydrous sodium acetate and 0.8 g of hydroxylamine hydrochloride. Then, the reaction was allowed to proceed at room temperature overnight. After completion of the reaction, water and ether were added to extract a reaction product. The organic layer was washed with water and dried over anhydrous sodium sulfate, followed by evaporation-removal of the ether under reduced pressure. As a result, there was obtained 3.5 g of a light yellow gummy substance composed of syn- and anti-isomers of 5-(2-chloro-4-trifluoromethylphenoxy)-α-methoxyacetophenone oxime. The NMR spectral data of this compound were as follows.

$^1$H-NMR spectral data [CDCl$_3$, δ(ppm)] 3.32 (s, 3H), 4.58 (s, 2H), 6.85–7.67 (m, 7H), 8.58 (s, 1H).

(b) 3.5 g of syn- and anti-isomers of 5-(2-chloro-4-trifluoromethylphenoxy)-α-methoxyacetophenone oxime obtained in step (a) above was dissolved in 20 ml of dried benzene. To the resulting solution was added 0.5 g of sodium hydride (in the form of an oil suspension at a concentration of about 60% by weight). The resulting mixture was stirred at room temperature for about 30 minutes until hydrogen gas was not generated any longer. Then, the mixture was cooled to 5° to 10° C., and to the mixture, 1.8 g of methyl bromoacetate was added, followed by stirring at 5° to 10° C. for 1 hour and, further, at room temperature overnight. After completion of the reaction, the reaction mixture was poured into ice-water, followed by addition of ether to extract a reaction product. The organic layer was washed with water, followed by evaporation-removal of the ether and benzene under reduced pressure to obtain a crude product. The thus obtained crude product was subjected to purification by the silica gel column chromatography. As a result, there was obtained 3.2 g of a light yellow gummy substance composed of syn- and anti-isomers of 5-(2-chloro-4-trifluoromethylphenoxy)-α-methoxyacetophenone oxime-O-(acetic acid, methyl ester).

(c) 3.5 g of syn- and anti-isomers of 5-(2-chloro-4-trifluoromethylphenoxy)-α-methoxyacetophenone oxime-O-(acetic acid, methyl ester) as prepared in step (b) above was dissolved in 30 ml of dichloromethane, and the solution was cooled to about 0° C. To the resulting solution, a mixed acid cooled at about 0° C. and composed of 8.6 g of concentrated sulfuric acid and 0.8 g of nitric acid (d:1.42) was dropwise added over a period of 15 minutes. After completion of the dropwise addition, the reaction was allowed to proceed at 0° C. to 5 ° C. for 30 minutes and, further, at room temperature for 1 hour. After completion of the reaction, the reaction mixture was poured into ice-water, followed by extraction with dichloromethane. The dichloromethane layer containing a reaction product was washed with water and dried over anhydrous sodium sulfate, followed by evaporation-removal of the dichloromethane under reduced pressure, thereby to obtain a crude product. The thus obtained crude product was subjected to purification by the silica gel column chromatography. As a result, there was obtained 2.6 g of a white gummy substance composed of syn- and anti-isomers of 5-(2-chloro-4-trifluoromethylphenoxy)-2-nitro-α-methoxyacetophenone oxime-)-O-(acetic acid, methyl ester). This substance was allowed to stand at room temperature to obtain a white solid having a melting point of 55° C. to 57° C.

EXAMPLE 4

Preparation of syn- and anti-isomers of 5-(2-chloro-4-trifluoromethylphenoxy)-2-nitro-α-methoxyacetophenone oxime-O-(acetic acid, methyl ester).: Compound No. 9

(a) 68.9 g of 3-(2-chloro-4-trifluoromethylphenoxy)-α-methoxyacetophenone as prepared in the same manner as in step (a) of Example 1 was dissolved in 600 ml of methanol. To the resulting solution were added 16.4 g of anhydrous sodium acetate and 43.7 g of carboxymethoxylamine.½hydrochloride, followed by heating under reflux for one hour. After completion of the reaction, the reaction mixture was cooled, the inorganic salt was filtered off, and the filtrate was subjected to evaporation-removal of most of the methanol under reduced pressure. Subsequently, water and dichloromethane were added to effect extraction. The dichloromethane layer was separated, washed with water and dried over anhydrous sodium sulfate, followed by evaporation-removal of dichloromethane under reduced pressure. As a result, there was obtained 79.3 g of light yellow crystals of 3-(2-chloro-4-trifluoromethylphenoxy)-α-methoxyacetophenone oxime-O-(acetic acid) having a melting point of 88° C. to 89° C. The NMR spectral data of this compound were given below.

$^1$H-NMR spectral data [CDCl$_3$, δ(ppm)] 3.33 (s,3H), 4.59 (s,2H), 4.71 (s,2H), 6.77–7.64 (m,7H), 10.88 (s,1H).

(b) 62.6 g of 3-(2-chloro-4-trifluoromethylphenoxy)-α-methoxyacetophenone oxime-O-(acetic acid) obtained in step (a) above was added to a mixture cooled to below 5° C. and composed of 300 ml of dichloromethane and 150 ml of concentrated sulfuric acid, followed by gradual addition of 15.2 g of potassium nitrate. The reaction was allowed to proceed at below 5 ° C for 1 hour, and the liquid reaction mixture was poured into ice-water. Then, 500 ml of dichloromethane was added to effect extraction. The dichloromethane layer was separated, washed with an aqueous sodium chloride saturated solution and with water, and dried over anhydrous sodium sulfate, followed by evaporation-removal of the dichloromethane under reduced pressure to obtain a crude product. The crude product thus obtained was subjected to purification by the silica gel column chromatography to obtain 45 g of white crystals composed of syn- and anti-isomers of 5-(2-chloro-4-trifluoromethylphenoxy)-2-nitro-α-methoxyacetophenone oxime-O-(acetic acid) (Compound 7) having a melting point of 100° C. to 102° C. The spectral data of this compound were given below.

$^1$H-NMR spectral data [CDCl$_3$, δ(ppm)] 3.18 and 3.35 (s,3H), 4.29 and 4.70 (s,2H), 4.55 (s,2H), 6.91–8.18 (m,6H), 10.15 (s,1H), (c) 4.6 g of syn- and anti-isomers of 5-(2-chloro-4-trifluoromethylphenoxy)-2-nitro-α-methoxyacetophenone oxime-O-(acetic acid) obtained in step (b) above was dissolved in 100 ml of methanol, followed by addition of a catalytic amount of p-toluenesulfonic acid. The resulting solution was heated under reflux for 5 hours. After completion of the reaction, the methanol was distilled off under reduced pressure. The residue obtained was dissolved in ethyl acetate, and the ethyl acetate layer was washed with water and dried over anhydous sodium sulfate, followed by evaporation-removal of the ethyl acetate under reduced pressure. As a result, there was obtained 4.8 g of a white gummy substance composed of syn- and anti-isomers of 5-(2-chloro-4-trifluoromethylphenoxy)-2-nitro-α-methoxyacetophenone oxime-O-(acetic acid, methyl ester). The substance thus obtained was allowed to stand at room temperature in the same manner as in Example 3, thereby to obtain white crystals having a melting point of 54° C. to 56° C.

EXAMPLE 5

Preparation of syn- and anti-isomers of 5-(2-chloro-4-trifluoromethylphenoxy)-2-nitro-α-methoxyacetophenone oxime-O-(acetic acid, phenyl ester): Compound No. 18

(a) 13.9 g of syn- and anti-isomers of 5-(2-chloro-4-trifluoromethylphenoxy)-2-nitro-α-methoxyacetophenone oxime-O-(acetic acid) obtained in substantially the same manner as in step (b) of Example 4 was dissolved in 100 ml of benzene. Then, 7.1 g of thionyl chloride was added thereto, and the resulting reaction mixture was heated under reflux for 8 hours. After completion of the reaction, the solvent was distilled off under reduced pressure to obtain 14.2 g of syn- and anti-isomers of 5-(2-chloro-4-trifluoromethylphenoxy)-2-nitro-α-methoxyacetophenone oxime-O-(acetyl chloride).

(b) 0.9 g of phenol was dissolved in 20 ml of dried benzene. Then, 0.5 g of sodium hydride (in the form of an oil suspension at a concentration of about 60% by weight) was added, and the resulting mixture was stirred at room temperature for about 30 minutes until hydrogen gas was not generated any longer, followed by cooling to 5° C. to 10° C. To the resulting solution was added 4.8 g of syn- and anti-isomers of 5-(2-chloro-4-trifluoromethylphenoxy)-2-nitro-α-methoxyacetophenoneoxime-O-(acetyl chloride) as obtained in step (a) above. Then, the reaction was allowed to proceed at room temperature overnight. After completion of the reaction, cold water and ether were added to extract a reaction product. The separated ether layer was washed with water and dried over anhydrous sodium sulfate. Then, the ether was distilled off under reduced pressure, thereby to obtain a crude product. The crude product thus obtained was subjected to purification by the silica gel column chromatography to obtain 3.5 g of a light yellow oily substance composed of syn- and anti-isomers of 5-(2-chloro-4-trifluoromethylphenoxy)-2-nitro-α-methoxyacetophenone oxime-O-(acetic acid, phenyl ester) having a refractive index $n_D^{30}$ of 1.5539.

EXAMPLE 6

Preparation of syn- and anti-isomers of 5-(2-chloro-4-trifluoromethylphenoxy)-2-nitro-α-methoxyacetophenone acetophenone oxime-O-(acetic acid, ethyl ester): Compound No. 10

1.9 g of 5-(2-chloro-4-trifluoromethylphenoxy)-2-nitro-α-methoxyacetophenone (Compound No. 51) as prepared in substantially the same manner as in Example 1 was dissolved in a mixture of 20 ml of anhydrous ethanol and 20 ml of dried benzene, followed by addition of 0.6 g of anhydrous sodium acetate and 1.2 g of O-ethoxycarbonylmethyl hydroxylamine hydrochloride. Then, the mixture was heated under reflux for 8 hours and then cooled, followed by addition of water and ether to extract a reaction product. The organic layer was washed with water and dried over sodium sulfate anhydride. Then, the ether and benzene were distilled off under reduced pressure, thereby to obtain a crude product. The crude product thus obtained was subjected to purification by the silica gel column chromatography. As a result, there was obtained 2.1 g of a light orange viscous oily substance (Compound No. 10) composed of syn- and anti-isomers of 5-(2-chloro-4-trifluoromethylphenoxy)-2-nitro-α-methoxyacetophenone oxime-O-(acetic acid, ethyl ester) having a refractive index $n_D^{30}$ of 1.5276.

EXAMPLE 7

Preparation of ethyl 2-[2-nitro-5-(2'-chloro-4'-trifluoromethylphenoxy)phenacyloxy]propionate: Compound No. 57

(a) 3.7 g of 2-[3-(2'-chloro-4'-trifluoromethylphenoxy)phenyl]-1,3-dioxolane-2-methanol was dissolved in 20 ml of dried N,N-dimethylacetamide, followed by addition of 0.48 g of sodium hydride (in the form of an oil suspension at a concentration of about 60% by weight) at room temperature. Then, the mixture was heated to 40° C. to 50° C. and stirred until hydrogen gas was not generated any longer. Subsequently, the mixture was cooled to about 0° C. and 2.2 g of ethyl 2-bromopropionate was dropwise added to the mixture After completion of the dropwise addition, the mixture was stirred at room temperature for 1 hour to complete the reaction. Then, the reaction mixture was poured into ice-water, followed by extraction twice with 30 ml portions of ether. The organic layer was separated, washed and dried by the customary method. Then, the ether was distilled off under reduced pressure to obtain a crude product. The crude product thus obtained was subjected to purification by the silica gel column chromatography to obtain 4 g of a colorless oily substance of 2-[3-(2'-chloro-4'-trifluromethylphenoxy)phenyl] -2-(1-ethoxycarbonylethoxy)methyl-1,3-dioxolane.

(b) 4 g of 2-[3-(2'-chloro-4'-trifluoromethylphenoxy)-phenyl]-2-(1-ethoxycarbonylethoxy)methyl-1,3-dioxolane obtained in step (a) above was dissolved in 20 ml of 1,2-dichloroethane, and then the solution was poured into 10 ml of concentrated sulfuric acid which had been cooled to 0° C. To the solution was dropwise added a cooled mixture of 4 g of concentrated sulfuric acid and 2 g of nitric acid (specific gravity: 1.42) while maintaining the temperature of the solution at below 5° C. Then, the reaction was further allowed to proceed by maintaining the temperature for 1.5 hours. After completion of the reaction, the reaction mixture was poured into ice-water, followed by extraction of the reaction product with 50 ml of 1,2-dichloroethane. According to the customary method, the organic layer was separated, washed with water, then with aqueous sodium bicarbonate solution, and further with water, and dried. Then, the 1,2-dichloroethane was distilled off under reduced pressure, thereby to obtain a crude product. The thus obtained crude product was subjected to purification by the silica gel column chromatography to obtain 2.4 g of a yellow oily substance of ethyl 2-[2-nitro-5-((2'-chloro-4'-trifluoromethylphenoxy)-phenacyloxy]propionate having a refractive index $n_D^{21.5}$ of 1.5300.

EXAMPLE 8

Preparation of syn- and anti-isomers of 5-(2-chloro-4-trifluoromethylphenoxy)-2-nitro-α-methoxyacetophenone oxime-O-(acetic acid, N-methyl-N-methoxyamide): Compound No. 45

To 10 ml of N,N-dimethylacetamide were added 0.2 g of N,O-dimethylhydroxylamine hydrochloride and 0.21 g of triethylamine. To the solution was dropwise added, at room temperature, 3 ml of a solution of N,N-dimethylacetamide containing 1 g of syn- and anti-isomers of 5-(2-chloro-4-trifluoromethylphenoxy)-2-nitro-α-methoxyacetophenone oxime-O-(acetyl chloride) as obtained in step (a) of Example 5. The reaction was allowed to proceed for 3 hours. After completion of the reaction, the reaction product was extracted with water and ether by the customary method. The ether layer was separated, washed with water and dried over anhydrous sodium sulfate. Then, the ether was distilled off under reduced pressure to obtain a crude product. The thus obtained crude product was subjected to purification by the silica gel column chromatography, thereby to obtain 0.7 g of light yellow crystals composed of syn- and anti-isomers of 5-(2-chloro-4-trifluoromethylphenoxy)-2-nitro-α-methoxyacetophenone oxime-O-(acetic acid, N-methyl-N-methoxyamide) having a melting point of 85° C. to 88° C.

EXAMPLE 9

Preparation of syn- and anti-isomers of 5-(2-chloro-4-trifluoromethylphenoxy)-2-nitro-α-methoxyacetophenone oxime-O-(acetic acid, ethyl ester): Compound No. 10

0.8 g of syn- and anti-isomers of 5-(2-chloro-4-trifluoromethylphenoxy)-2-nitro-α-methoxyacetophenone oxime prepared in substantially the same manner as in Example 2 were dissolved in a mixture of 10 ml of dried benzene and 10 ml of dried N,N-dimethylacetamide. To the solution was added 0.1 g of sodium hydride (in the form of an oil suspension at a concentration of about 60% by weight). Then, the mixture was stirred at room temperature for 30 minutes until hydrogen gas was not generated any longer. Subsequently, the mixture was cooled to 5° to 10° C., followed by addition of 0.4 g of ethyl bromoacetate. Then, the mixture was stirred at 5° to 10° C. for 1 hour and, further, at room temperature overnight. After completion of the reaction, the reaction mixture was poured into ice-water, followed by addition of ether to extract the reaction product. The organic layer was washed with water, and the ether and benzene were distilled off under reduced pressure to obtain a crude product. The thus obtained crude product was subjected to purification by the silica gel column chromatography to obtain 0.68 g of a light orange viscous oily substance (Compound No. 10) composed of syn- and anti-isomers of 5-(2-chloro-4-trifluoromethylphenoxy)-2-nitro-α-methoxyacetophenone oxime-O-(acetic acid, ethyl ester).

EXAMPLE 10

In substantially the same manner as in the above Examples, various compounds of the present invention were prepared. The structures, physical properties and $^1$H-NMR analysis data of these compounds are shown in Tables 1 and 2, together with those of the compounds prepared in Examples 1 to 9. However, it should be understood that the scope of the present invention is by no means limited to these compounds.

TABLE 1

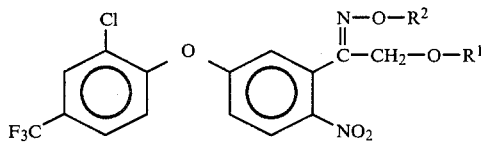

| Compound No. | R$^1$ | R$^2$ | Physical Properties | $^1$H—NMR Spectral Data (δ: CDCl$_3$) |
|---|---|---|---|---|
| 1 | —CH$_3$ | —H (syn) | mp (°C.) 123~125 | 2.53(DMSO), 3.12(s, 3H), 4.40(s, 2H), 6.98~8.08(m, 6H), 11.39(s, 1H) |
| 2 | —CH$_3$ | —H (anti) | $n_D^{30}$ 1.5278 | 2.53(DMSO), 3.31(s, 3H), 4.25(s, 2H), 6.93~8.13(m, 6H), 11.08(s, 1H) |
| 3 | —CH$_3$ | —CH$_3$ | mp (°C.) 81~82 | 3.18 and 3.37(s, 3H), 3.79 and 3.97 (s, 3H), 4.30 and 4.43(s, 2H) 6.89~8.16(m, 6H) |
| 4 | —CH$_3$ | —C$_2$H$_5$ | $n_D^{30}$ 1.5255 | 1.16 and 1.25(t, 3H), 3.09 and 3.30 (s, 3H), 3.93 and 4.10(q, 2H), 4.17 and 4.36(s, 2H), 6.72~7.97(m, 6H) |
| 5 | —CH$_3$ | —C$_3$H$_7$(n) | $n_D^{30}$ 1.5279 | 0.75 and 0.92(t, 3H), 1.20~1.83(m, 2H) 3.09 and 3.29(s, 3H), 3.87 and 4.03 (t, 2H), 4.21 and 4.36(s, 2H), 6.74~8.03(m, 6H) |
| 6 | —CH$_3$ | —C$_3$H$_7$(i) | $n_D^{30}$ 1.5279 | 1.07 and 1.26(d, 6H), 3.09 and 3.32 (s, 3H), 4.20 and 4.34(s, 2H), 3.88~4.52(m, 1H), 6.68~7.99(m, 6H) |
| 7 | —CH$_3$ | —CH$_2$COOH | mp (°C.) 100~102 | 3.18 and 3.35(s, 3H), 4.29 and 4.70 (s, 2H), 4.55(s, 2H), 6.91~8.18(m, 6H), 10.15(s, 1H) |
| 8 | —CH$_3$ | —CH$_2$COONa | mp (°C.) | DMSO—d$_6$ |

TABLE 1-continued

Structure:
2-chloro-4-(trifluoromethyl)phenoxy group connected via ether to a phenyl ring bearing NO2 and a C(=N-O-R²)-CH2-O-R¹ substituent.

| Compound No. | R¹ | R² | Physical Properties | ¹H—NMR Spectral Data (δ: CDCl₃) |
|---|---|---|---|---|
| 9 | —CH₃ | —CH₂COOCH₃ | 95~105 (Decomposed) mp (°C.) 55~57 | 3.12 and 3.29(s, 3H), 4.13 and 4.46 (s, 2H), 4.26(s, 2H), 7.03~8.29(m, 6H) 3.17 and 3.32(s, 3H), 3.67 and 3.72 (s, 3H), 4.26 and 4.67(s, 2H), 4.52(s, 2H), 6.82~8.23(m, 6H) |
| 10 | —CH₃ | —CH₂COOC₂H₅ | $n_D^{30}$ 1.5276 | 1.23 and 1.26(t, 3H), 3.15 and 3.32 (s, 3H), 4.11 and 4.14(q, 2H), 4.23 and 4.62(s, 2H), 4.49(s, 2H), 6.77~8.20(m, 6H) |
| 11 | —CH₃ | —CH₂COOC₃H₇(n) | $n_D^{30}$ 1.5219 | 0.87 and 0.90(t, 3H), 1.22~1.93(m, 2H), 3.13 and 3.30(s, 3H), 3.99 and 4.03 (t, 2H), 4.23 and 4.61(s, 2H), 4.48(s, 2H), 6.78~8.11(m, 6H) |
| 12 | —CH₃ | —CH₂COOH·NH₂—CH₃ | Brown gummy substance | 2.39(s, 3H), 3.08 and 3.30(s, 3H), 4.22 and 4.53(s, 2H), 4.33(s, 2H), 6.78~7.06(m, 6H) 9.00(bs, 3H) |
| 13 | —CH₃ | —CH(CH₃)COOCH₃ | $n_D^{30}$ 1.5200 | 1.30 and 1.49(d, 3H), 3.15 and 3.28 (s, 3H), 3.62 and 3.66(s, 3H), 4.22 and 4.47(s, 2H), 4.63 and 4.73 (q, 1H), 6.77~8.13(m, 6H) |
| 14 | —CH₃ | —CH(CH₃)COOC₂H₅ | $n_D^{30}$ 1.5135 | 1.21(t, 3H), 1.30 and 1.49(d, 3H), 3.13 and 3.27(s, 3H), 4.05 and 4.10 (q, 2H), 4.20 and 4.44(s, 2H), 4.57 and 4.55(q, 1H), 6.82~8.13(m, 6H) |
| 15 | —CH₃ | —CH₂COOCH₂CH=CH₂ | mp (°C.) 58~59 | 3.30(s, 3H), 4.23(s, 2H), 4.51(s, 2H), 4.51~6.15(m, 3H), 6.82~8.13(m, 6H) |
| 16 | —CH₃ | —CH₂COOC(CH₃)=CH₂ | mp (°C.) 48.5~49.5 | 1.71(s, 3H), 3.14 and 3.30(s, 3H), 4.23 and 46.5(s, 2H), 4.46 and 4.53 (s, 4H), 4.85(m, 2H), 6.80~8.13(m, 6H) |
| 17 | —CH₃ | —CH₂COOCH₂C≡CH | mp (°C.) 79~80 | 2.43(m, 1H), 3.30(s, 3H), 4.22(s, 2H), 4.51(s, 2H), 4.61(d, 2H), 6.81~8.12(m, 6H) |
| 18 | —CH₃ | —CH₂COO—C₆H₅ | $n_D^{30}$ 1.5539 | 3.13 and 3.29(s, 3H), 4.25 and 4.62 (s, 2H), 4.47 and 4.72(s, 2H), 6.82~8.13(m, 11H) |
| 19 | —CH₃ | —CH₂COO—C₆H₄—OCH₃ | $n_D^{30}$ 1.5570 | 3.16(s, 3H), 3.73(s, 3H), 4.53(3, 2H), 4.88(s, 2H), 6.80~8.07(m, 10H) |
| 20 | —CH₃ | —CH₂COOCH₂CH₂Cl | $n_D^{30}$ 1.5321 | 3.17 and 3.33(s, 3H), 3.55 3.73(m, 2H), 4.27 and 4.70(s, 2H), 4.27~4.42(m, 2H), 4.57(s, 2H), 6.86~8.20(m, 6H) |
| 21 | —CH₃ | —CH₂COOCH₂CH₂OCH₃ | $n_D^{30}$ 1.5218 | 3.09 and 3.27(s, 6H), 3.38~3.55(m, 2H), 4.06~4.22(m, 2H), 4.18 and 4.62(s, 2H), 4.48(s, 2H), 6.82~8.11(m, 6H) |
| 22 | —CH₃ | —CH₂COOCH(CH₃)CH₂OCH₃ | $n_D^{30}$ 1.5178 | 1.20(d, 3H), 3.32(s, 6H), 3.33(d, 2H), 4.26(s, 2H), 4.51(s, 2H), 5.03(q, 1H), 6.83~8.14(m, 6H) |
| 23 | —CH₃ | —CH₂COOCH₂COOCH₃ | $n_D^{30}$ 1.5220 | 3.27(s, 3H), 3.68(s, 3H), 4.20(s, 2H), 4.55(s, 2H), 4.58(s, 2H), 6.89~8.12 (m, 6H) |
| 24 | —CH₃ | —CH₂COOCH₂COOC₂H₅ | $n_D^{30}$ 1.5177 | 1.25(t, 3H), 3.28(s, 3H), 4.13(q, 2H), 4.23(s, 2H), 4.55(s, 2H), 4.58(s, 2H), 6.87~8.15(m, 6H) |
| 25 | —CH₃ | —CH₂COOCH(CH₃)COOCH₃ | $n_D^{30}$ 1.5176 | 1.47(d, 3H), 3.30(s, 3H), 3.69(s, 3H), 4.25(s, 2H), 4.59(s, 2H), 5.09(q, 1H), 6.89~8.18(m, 6H) |
| 26 | —CH₃ | —CH₂COOCH(CH₃)COOC₂H₅ | $n_D^{30}$ 1.5179 | 1.32(t, 3H), 1.54(d, 3H), 3.40(s, 3H), 4.23(q, 2H), 4.34(s, 2H), 4.67(s, 2H), 5.14(q, 1H), 6.88~8.28(m, 6H) |

TABLE 1-continued

[Structure: 2-chloro-4-(trifluoromethyl)phenyl ether linked to phenyl ring bearing NO₂ and C(=N–O–R²)–CH₂–O–R¹ group]

| Compound No. | R¹ | R² | Physical Properties | ¹H—NMR Spectral Data (δ: CDCl₃) |
|---|---|---|---|---|
| 27 | —CH₃ | —CH(CH₃)COOCH₂CH=CH₂ | $n_D^{30}$ 1.5259 | 1.31 and 1.52(d, 3H), 3.12 and 3.26 (s, 3H), 4.19 and 4.69(s, 2H), 4.45(s, 2H), 4.41~6.17(m, 4H), 6.73~8.07(m, 6H) |
| 28 | —CH₃ | —CH(CH₃)COOCH₂C(CH₃)=CH₂ | $n_D^{30}$ 1.5272 | 1.32 and 1.52(d, 3H), 1.70(bs, 3H), 3.12 and 3.26(s, 3H), 4.18 and 4.56 (s, 2H), 4.43(s, 2H), 4.43~4.81(m, 3H), 6.73~8.08(m, 6H) |
| 29 | —CH₃ | —CH(CH₃)COOCH₂C≡CH | $n_D^{30}$ 1.5294 | 1.32 and 1.52(d, 3H), 2.35~2.43(m, 1H), 3.13 and 3.27(s, 3H), 4.20 and 4.47 (s, 2H), 4.57~4.83(m, 3H), 6.77~8.10(m, 6H) |
| 30 | —CH₃ | —CH(CH₃)COOCH₂CH₂OCH₃ | $n_D^{30}$ 1.5221 | 1.32 and 1.52(d, 3H), 3.16 and 3.29 (s, 3H), 3.32(s, 3H), 3.43~3.60(m, 2H), 4.10~4.23(m, 2H), 4.23 and 4.49(s, 2H), 4.49~4.85(m, 1H), 6.80~8.15(m, 6H) |
| 31 | —CH₃ | —CH(CH₃)COOCH₂COOCH₃ | $n_D^{30}$ 1.5222 | 1.37 and 1.61(d, 3H), 3.13 and 3.26 (s, 3H), 3.67(s, 3H), 4.20 and 4.48 (s, 2H), 4.59(s, 2H), 4.52~4.92(m, 1H), 6.78~8.24(m, 6H) |
| 32 | —CH₃ | —CH(CH₃)COOCH₂COOC₂H₅ | $n_D^{30}$ 1.5191 | 1.24(t, 3H), 1.38 and 1.58(d, 3H), 3.13 and 3.27(s, 3H), 4.13(q, 2H), 4.22 and 4.52(s, 2H), 4.56~4.93(m, 3H), 6.80~8.14(m, 6H) |
| 33 | —CH₃ | —CH(CH₃)COOCH(CH₃)COOCH₃ | $n_D^{30}$ 1.5155 | 1.37 and 1.48 and 1.59(d, 6H), 3.15 and 3.30(s, 3H), 3.69(s, 3H), 4.24 and 4.62(s, 2H), 4.56~5.25(m, 2H), 6.82~8.17(m, 6H) |
| 34 | —CH₃ | —CH(CH₃)COOCH(CH₃)COOC₂H₅ | $n_D^{30}$ 1.5106 | 1.24(t, 3H), 1.38 and 1.48 and 1.58(d, 6H), 3.15 and 3.29(s, 3H), 4.18(q, 2H), 4.28 and 4.66 (s, 2H), 4.60~5.27(m, 2H), 6.88~8.22(m, 6H) |
| 35 | —CH₃ | —CH₂COSCH₃ | mp (°C.) 70~72 | 2.20(s, 3H), 3.15 and 3.31(s, 3H), 4.25 and 4.69(s, 2H), 4.47 and 4.55(s, 2H), 6.80~8.17(m, 6H) |
| 36 | —CH₃ | —CH₂COSC₂H₅ | mp (°C.) 61.5~62.5 | 1.18(t, 3H), 2.78(q, 2H), 3.14 and 3.29 (s, 3H), 4.23 and 4.59(s, 2H), 4.45 and 4.52 (s, 2H), 6.86~8.13(m, 6H) |
| 37 | —CH₃ | —CH₂COSCH₂CH=CH₂ | mp (°C.) 52~55 | 3.15 and 3.31(s, 3H), 3.44(d, 2H), 4.26 and 4.51(s, 2H), 4.57(s, 2H), 4.91~6.04(m, 3H), 6.90~8.19(m, 6H) |
| 38 | —CH₃ | —CH₂COSCH₂COOCH₃ | $n_D^{30}$ 1.5478 | 3.17 and 3.32(s, 3H), 3.60 and 3.67(s, 5H), 4.26 and 4.54(s, 2H), 4.49 and 4.62(s, 2H) 6.85~8.20(m, 6H) |
| 39 | —CH₃ | —CH(CH₃)COSCH₃ | $n_D^{30}$ 1.5395 | 1.28 and 1.50(d, 3H), 2.15(s, 3H), 3.13 and 3.29(s, 3H), 4.23 and 4.57(s, 2H), 4.49~4.84 (m, 1H), 6.82~8.16(m, 6H) |
| 40 | —CH₃ | —CH(CH₃)COSCH₂COOCH₃ | $n_D^{30}$ 1.5367 | 1.31 and 1.52(d, 3H), 3.17 and 3.31(s, 3H), 3.55 and 3.62(s, 2H), 3.67(s, 3H), 4.25 and 4.53(s, 2H), 6.82~8.17(m, 6H) |
| 41 | —CH₃ | —CH₂C(O)NH₂ | Gummy substance | 3.14 and 3.29(s, 3H), 4.20 and 4.52(s, 2H), 4.38(s, 2H), 5.97(b, 2H), 6.70~8.05(m, 6H) |
| 42 | —CH₃ | —CH₂C(O)NHCH₃ | Gummy substance | 2.82(d, 3H), 3.20 and 3.31(s, 3H), 4.23 and 4.58(s, 2H), 4.43 and 4.48(s, 2H), 6.27(m, 1H), 6.80~8.14(m, 6H) |
| 43 | —CH₃ | —CH₂C(O)NHC(CH₃)₂C≡CH | Gummy substance | 1.63(s, 6H), 3.19 and 3.32(s, 3H), 4.22 and 4.50(s, 2H), 4.35 and 4.42(s, 2H), 6.22(b, 1H), 6.80~8.15(m, 6H) |
| 44 | —CH₃ | —CH₂C(O)N(CH₃)₂ | Gummy substance | 2.83 and 2.90 and 2.97(s, 6H), 3.16 and 3.28 (s, 3H), 4.22 and 4.75(s, 2H), 4.48 and 4.58 (s, 2H), 6.76~8.09(m, 6H) |

TABLE 1-continued $$\text{structure: 2-Cl, 4-CF}_3\text{-phenyl-O-phenyl(2-NO}_2\text{)-C(=N-O-R}^2\text{)-CH}_2\text{-O-R}^1$$

| Compound No. | R¹ | R² | Physical Properties | ¹H—NMR Spectral Data (δ: CDCl₃) |
|---|---|---|---|---|
| 45 | —CH₃ | —CH₂CN(=O)(CH₃)(OCH₃) | mp (°C.) 85~88 | 3.17 and 3.28(s, 6H), 3.67(s, 3H), 4.23 and 4.86(s, 2H), 4.53 and 4.70(s, 2H), 6.77~8.13(m, 6H) |
| 46 | —CH₃ | —CHCONH₂ (with CH₃) | Gummy substance | 1.32 and 1.52(d, 3H), 3.17 and 3.30(s, 3H), 4.23 and 4.44(s, 2H), 3.30~3.72(m, 1H), 5.88(b, 2H), 6.78~8.13(m, 6H) |
| 47 | —CH₃ | —CHCONHCH₃ (with CH₃) | Gummy substance | 1.32 and 1.51(d, 3H), 2.78 and 2.82(d, 3H), 3.22 and 3.33(s, 3H), 4.23 and 4.48(s, 2H), 4.42~4.85(m, 1H), 5.97(b, 1H), 6.83~8.20(m, 6H) |
| 48 | —CH₃ | —CHCON(CH₃)(OCH₃) (with CH₃) | Gummy substance | 1.23 and 1.44(d, 3H), 3.08 and 3.13(s, 3H), 3.13 and 3.25(s, 2H), 3.63(s, 3H), 4.20 and 4.48(s, 2H), 4.83~5.27(m, 1H), 6.78~8.08(m, 6H) |
| 49 | —CHCOOCH₃ (with CH₃) | —H | $n_D^{25}$ 1.5378 | 1.17 and 1.27(d, 3H), 3.63(s, 3H), 3.80 and 3.91(q, 1H), 4.31 and 4.37 and 4.50 and 4.59 (s, 2H), 6.80~8.09(m, 6H), 8.58 and 8.82 (bs, 1H) |
| 50 | —CHCOOC₂H₅ (with CH₃) | —H | $n_D^{25}$ 1.5388 | 1.18 and 1.29(d, 3H), 1.24(t, 3H), 3.82 and 4.11(q, 3H), 4.36 and 4.42 and 4.55 and 4.65 (s, 2H), 6.85~8.17(m, 6H), 8.50(b, 1H) | s: singlet, d: doublet, t: triplet, m: multiplet, b: broad, q: quartet

TABLE 2

$$\text{structure: 2-Cl, 4-CF}_3\text{-phenyl-O-phenyl(2-NO}_2\text{)-C(=O)-CH}_2\text{-O-R}^1$$

| Compound No. | R¹ | Physical Properties | ¹H—NMR Spectral Data (δ: CDCl₃) |
|---|---|---|---|
| 51 | —CH₃ | mp (°C.) 95~96 | 3.39(s, 3H), 4.28(s, 2H), 6.85~8.20(m, 6H) |
| 52 | —CH₂COOH | mp (°C.) 35~37 | 4.16(s, 2H), 4.48(s, 2H), 6.84~8.13(m, 6H), 10.33(bs, 1H) |
| 53 | —CH₂COOCH₃ | $n_D^{21.5}$ 1.5465 | 3.67(s, 3H), 4.08(s, 2H), 4.44(s, 2H), 6.83~8.13(m, 6H) |
| 54 | —CH₂COOC₂H₅ | $n_D^{30}$ 1.5105 | 1.25(t, 3H), 4.10(s, 2H), 4.17(q, 2H), 4.48(s, 2H), 6.87~8.20(m, 6H) |
| 55 | —CH₂COOC₃H₇(n) | $n_D^{23}$ 1.5300 | 0.91(t, 3H), 1.56(q, 2H), 4.03(t, 2H), 4.06(s, 2H), 4.46(s, 2H), 6.86~8.14(m, 6H) |
| 56 | —CHCOOCH₃ (with CH₃) | $n_D^{30}$ 1.5190 | 1.31(d, 3H), 3.67(s, 3H), 4.02(q, 1H), 4.42(d, 2H), 6.85~8.14(m, 6H) |
| 57 | —CHCOOC₂H₅ (with CH₃) | $n_D^{21.5}$ 1.5300 | 1.20(t, 3H), 1.26(d, 3H), 3.90(q, 1H), 4.07(q, 2H), 4.33(d, 2H), 6.78~8.09(m, 6H) |
| 58 | —CHCOOC₃H₇(n) (with CH₃) | $n_D^{30}$ 1.5253 | 1.92(t, 3H), 1.28(d, 3H), 1.64(m, 2H), 3.98(q, 1H), 4.03(t, 2H), 4.37 and 4.42(s, 2H), 6.86~8.13(m, 6H) |
| 59 | —CHCOOC₄H₉(n) (with CH₃) | $n_D^{30}$ 1.5221 | 0.80~1.08(m, 3H), 1.29(d, 3H), 1.30~1.74(m, 4H), 3.98(q, 1H), 4.08(t, 2H), 4.38 and 4.42(s, 2H), 6.87~8.16(m, 6H) |
| 60 | —CH₂COOCH₂CH₂OCH₃ | $n_D^{30}$ 1.5230 | 3.29(s, 3H), 3.45~3.61(m, 2H), 4.11(s, 2H), 4.11~4.29(m, 2H), 4.45(s, 2H), 6.89~8.15(m, 6H) |
| 61 | —CH₂COOCH₂CH=CH₂ | Gummy substance | 4.13(s, 2H), 4.44(s, 2H), 4.53~6.21(m, 5H), 6.87~8.18(m, 6H) |
| 62 | —CH₂COOCH₂C≡CH | $n_D^{30}$ 1.5410 | 2.46~2.53(m, 1H), 4.17(s, 2H), 4.50(s, 2H), 4.69(d, 2H), 6.90~8.19(m, 6H) |
| 63 | —CH₂COOCH₂COOC₂H₅ | Gummy substance | 1.25(t, 3H), 4.17(q, 2H), 4.22(s, 2H), |

TABLE 2-continued $$\text{structure: 2-Cl-4-CF}_3\text{-phenyl-O-phenyl(2-NO}_2\text{)-C(=O)-CH}_2\text{-O-R}^1$$

| Compound No. | R¹ | Physical Properties | ¹H—NMR Spectral Data (δ: CDCl₃) |
|---|---|---|---|
| | | | 4.50(s, 2H), 4.60(s, 2H), 6.90~8.17(m, 6H) |
| 64 | —CH₂COOCH(CH₃)COOCH₃ | Gummy substance | 1.42(d, 3H), 3.63(s, 3H), 4.11(s, 2H), 4.43(s, 2H), 5.05(q, 1H), 6.81~8.11(m, 6H) |
| 65 | —CH(CH₃)COOCH₂CH₂Cl | $n_D^{30}$ 1.5266 | 1.33(d, 3H), 3.57~3.75(m, 2H), 4.05(q, 1H), 4.23~4.43(m, 2H), 4.42(d, 2H), 6.85~8.15(m, 6H) |
| 66 | —CH(CH₃)COOCH₂CH₂OCH₃ | $n_D^{30}$ 1.5231 | 1.31(d, 3H), 3.31(s, 3H), 3.46~3.61(m, 2H), 4.01(q, 1H), 4.13~4.32(m, 2H), 4.39(d, 2H), 4.86~8.14(m, 6H) |
| 67 | —CH(CH₃)COOCH(CH₃)CH₂OCH₃ | $n_D^{30}$ 1.5165 | 1.22(d, 3H), 1.30(d, 3H), 3.30(s, 3H), 3.98(q, 1H), 4.40(d, 2H), 5.08(q, 1H), 6.89~8.17(m, 6H) |
| 68 | —CH(CH₃)COOCH₂CH=CH₂ | Gummy substance | 1.32(d, 3H), 4.03(q, 1H), 4.41(d, 2H), 4.58 (d, 2H), 5.08~6.22(m, 3H), 6.87~8.19(m, 6H) |
| 69 | —CH(CH₃)COOCH₂C≡CH | $n_D^{30}$ 1.5337 | 1.33(d, 3H), 2.40~2.48(m, 1H), 4.03(q, 1H), 4.40(s, 2H), 4.62(d, 2H), 6.83~8.17(m, 6H) |
| 70 | —CH(CH₃)COOCH₂COOCH₃ | $n_D^{30}$ 1.5220 | 1.34(d, 3H), 3.70(s, 3H), 4.08(q, 1H), 4.42(d, 2H), 4.59(s, 2H), 6.87~8.12(m, 6H) |
| 71 | —CH(CH₃)COOCH(CH₃)COOCH₃ | $n_D^{30}$ 1.5185 | 1.33(d, 3H), 1.48(d, 3H), 3.70(s, 3H), 4.08(q, 1H), 4.43(d, 2H), 5.07(q, 1H), 6.87~8.18(m, 6H) |
| 72 | —CH(CH₃)COSCH₂CH=CH₂ | $n_D^{30}$ 1.5520 | 1.27(d, 3H), 3.42(d, 2H), 3.97(q, 1H), 4.43(s, 2H), 4.95~6.09(m, 3H), 6.85~8.22(m, 6H) |
| 73 | —CH(CH₃)COSCH₂COOCH₃ | Gummy substance | 1.30(d, 3H), 3.68(s, 3H), 3.73(s, 2H), 4.04(q, 1H), 4.46(s, 2H), 6.84~8.20(m, 6H) | s: singlet,
d: doublet,
t: triplet,
m: multiplet,
b: broad,
q: quartet

APPLICATION EXAMPLE

There will be given below some preparation examples for the herbicidal compositions according to the present invention.

PREPARATION EXAMPLE 1 (WETTABLE POWDER)

25 Parts by weight of the compound of the present invention, 5 parts by weight of Sorpol 5039 (trade name of a product of Toho Chemical Industry Company, Japan) and 70 parts by weight of talc are thoroughly pulverized and mixed to obtain wettable powder.

PREPARATION EXAMPLE 2 (EMULSIFIABLE CONCENTRATE)

5 Parts by weight of the compound of the present invention, 10 parts by weight of Sorpol 3005 X (a product of Toho Chemical Industry Company, Japan), 45 parts by weight of n-butanol and 40 parts by weight of xylene are thoroughly mixed to obtain emulsifiable concentrate.

PREPARTION EXAMPLE 3 (granule)

1 Part by weight of the compound of the present invention, 45 parts by weight of bentonite, 44 parts by weight of clay, 5 parts by weight of sodium lignosulfonate and 5 parts by weight of sodium dodecylbenzenesulfonate are thoroughly pulverized and mixed. To the mixture is added water, and the resultant is thoroughly kneaded. The kneaded mixture is then subjected to granulation, followed by drying, thereby to obtain granule.

PREPARTION EXAMPLE 4 (DUST)

1 Part by weight of the compound of the present invention and 99 parts by weight of clay are thoroughly pulverized and mixed to obtain dust.

APPLICATION EXAMPLE 1

Pots each having a surface area of 1/2500 a were packed with upland soil in a greenhouse. In each pot were planted seeds of soybean, Indian corn, crabgrass, velvetleaf, lambsquarter and smartweed.

The preemergence application was effected, by applying a composition in a dosage of 25 a.i. g/10a, 24 hours after the planting of the seeds. On the other hand, the postemergence application was effected by applying a composition in a dosage of 10 a.i. g/10a, when the soybean, the Indian corn and the weeds grew up to respectively 2 to 3 leaf stage, 3 to 4 leaf stage and 2 to 2.5 leaf stage. The herbicidal composition of the present invention was applied as follows. Using the compounds listed in Table 3, emulsifiable concentrates were prepared according to the method described in Preparation Example 2. Each of the thus prepared concentrates was diluted with 10 liters of water per each are of the upland soil, and then applied by means of a glass sprayer. 14 Days after the application, the degree of the herbicidal effect on weeds was observed. 30 Days after the application, the degree of the phytotoxicity to crop plants was observed. The results obtained are shown in Table 3. The values indicated in Table 3 are based on the following criterion.

5: Perfect inhibition
4: 80% inhibition
3: 60% inhibition
2: 40% inhibition
1: 20% inhibition
0: No effect

TABLE 3

| | Herbicidal Activity and Phytotoxicity | | | | | | | | | | | |
|---|---|---|---|---|---|---|---|---|---|---|---|---|
| | Preemergence application | | | | | | Postemergence application | | | | | |
| Compound No. | Crab- grass | Velvet- leaf | Lambs- quarter | Smart- weed | Soy- bean | Indian corn | Crab- grass | Velvet- leaf | Lambs- quarter | Smart- weed | Soy- bean | Indian corn |
| 1 | 2 | 4 | 4 | 4 | 0 | 0 | 1 | 4 | 4 | 4 | 0 | 0 |
| 2 | 1 | 4 | 4 | 4 | 0 | 0 | 1 | 4 | 3 | 3 | 0 | 0 |
| 3 | 3 | 5 | 5 | 4 | 0 | 0 | 2 | 5 | 4 | 4 | 1 | 0 |
| 4 | 2 | 4 | 4 | 4 | 0 | 0 | 1 | 5 | 3 | 4 | 0 | 0 |
| 5 | 1 | 4 | 3 | 4 | 0 | 0 | 1 | 4 | 3 | 4 | 0 | 0 |
| 6 | 1 | 4 | 3 | 3 | 0 | 0 | 1 | 4 | 3 | 3 | 0 | 0 |
| 7 | 2 | 4 | 4 | 4 | 0 | 0 | 1 | 4 | 4 | 3 | 0 | 0 |
| 8 | 2 | 4 | 3 | 4 | 0 | 0 | 1 | 4 | 4 | 3 | 0 | 0 |
| 9 | 4 | 5 | 5 | 5 | 0 | 0 | 4 | 5 | 5 | 5 | 1 | 0 |
| 10 | 4 | 5 | 5 | 5 | 0 | 0 | 4 | 5 | 5 | 5 | 1 | 0 |
| 11 | 4 | 5 | 4 | 5 | 0 | 0 | 2 | 5 | 5 | 5 | 0 | 0 |
| 12 | 2 | 4 | 3 | 4 | 0 | 0 | 1 | 4 | 4 | 3 | 0 | 0 |
| 13 | 3 | 5 | 4 | 5 | 0 | 0 | 3 | 5 | 5 | 5 | 1 | 0 |
| 14 | 3 | 5 | 4 | 4 | 0 | 0 | 2 | 5 | 4 | 5 | 0 | 0 |
| 15 | 3 | 5 | 5 | 5 | 0 | 0 | 4 | 5 | 5 | 5 | 0 | 0 |
| 16 | 2 | 4 | 5 | 5 | 0 | 0 | 1 | 5 | 3 | 4 | 0 | 0 |
| 17 | 3 | 5 | 5 | 5 | 0 | 0 | 3 | 5 | 5 | 5 | 0 | 0 |
| 18 | 3 | 4 | 4 | 5 | 0 | 0 | 2 | 5 | 4 | 4 | 0 | 0 |
| 19 | 2 | 4 | 4 | 4 | 0 | 0 | 2 | 5 | 4 | 3 | 0 | 0 |
| 20 | 2 | 5 | 5 | 4 | 0 | 0 | 1 | 5 | 5 | 4 | 0 | 0 |
| 21 | 3 | 5 | 5 | 5 | 0 | 0 | 2 | 5 | 5 | 5 | 0 | 0 |
| 22 | 2 | 5 | 4 | 4 | 0 | 0 | 1 | 5 | 5 | 4 | 0 | 0 |
| 23 | 2 | 5 | 5 | 5 | 0 | 0 | 1 | 5 | 5 | 5 | 0 | 0 |
| 24 | 2 | 5 | 5 | 5 | 0 | 0 | 1 | 5 | 4 | 5 | 0 | 0 |
| 25 | 2 | 5 | 4 | 5 | 0 | 0 | 1 | 5 | 4 | 5 | 0 | 0 |
| 26 | 1 | 5 | 4 | 5 | 0 | 0 | 1 | 5 | 4 | 5 | 0 | 0 |
| 27 | 3 | 5 | 5 | 5 | 0 | 0 | 4 | 5 | 5 | 5 | 0 | 0 |
| 28 | 2 | 5 | 5 | 4 | 0 | 0 | 1 | 5 | 4 | 5 | 0 | 0 |
| 29 | 2 | 4 | 5 | 4 | 0 | 0 | 1 | 5 | 5 | 4 | 0 | 0 |
| 30 | 2 | 5 | 4 | 4 | 0 | 0 | 1 | 5 | 4 | 5 | 0 | 0 |
| 31 | 2 | 5 | 5 | 5 | 0 | 0 | 0 | 5 | 5 | 5 | 0 | 0 |
| 32 | 2 | 4 | 4 | 4 | 0 | 0 | 0 | 5 | 4 | 4 | 0 | 0 |
| 33 | 2 | 4 | 4 | 5 | 0 | 0 | 1 | 5 | 4 | 5 | 0 | 0 |
| 34 | 1 | 4 | 3 | 3 | 0 | 0 | 0 | 5 | 3 | 4 | 0 | 0 |
| 35 | 2 | 4 | 4 | 3 | 0 | 0 | 3 | 5 | 4 | 5 | 0 | 0 |
| 36 | 2 | 4 | 4 | 3 | 0 | 0 | 1 | 5 | 4 | 4 | 0 | 0 |
| 37 | 2 | 5 | 4 | 5 | 0 | 0 | 2 | 5 | 4 | 5 | 0 | 0 |
| 38 | 1 | 4 | 4 | 4 | 0 | 0 | 1 | 5 | 4 | 5 | 0 | 0 |
| 39 | 1 | 4 | 3 | 4 | 0 | 0 | 2 | 5 | 4 | 4 | 0 | 0 |
| 40 | 1 | 4 | 3 | 4 | 0 | 0 | 1 | 5 | 4 | 4 | 0 | 0 |
| 41 | 2 | 5 | 4 | 3 | 0 | 0 | 1 | 5 | 4 | 4 | 0 | 0 |
| 42 | 2 | 5 | 4 | 4 | 0 | 0 | 1 | 5 | 4 | 4 | 0 | 0 |
| 43 | 3 | 5 | 4 | 4 | 0 | 0 | 2 | 5 | 5 | 4 | 0 | 0 |
| 44 | 1 | 5 | 4 | 3 | 0 | 0 | 1 | 5 | 4 | 3 | 0 | 0 |
| 45 | 2 | 5 | 5 | 4 | 0 | 0 | 1 | 5 | 5 | 4 | 0 | 0 |
| 46 | 1 | 4 | 3 | 3 | 0 | 0 | 1 | 4 | 3 | 3 | 0 | 0 |
| 47 | 1 | 4 | 3 | 3 | 0 | 0 | 1 | 4 | 3 | 3 | 0 | 0 |
| 48 | 1 | 4 | 4 | 3 | 0 | 0 | 1 | 5 | 4 | 4 | 0 | 0 |
| 49 | 2 | 5 | 4 | 5 | 0 | 0 | 4 | 5 | 5 | 5 | 0 | 0 |
| 50 | 2 | 5 | 4 | 5 | 0 | 0 | 4 | 5 | 5 | 5 | 1 | 0 |
| 51 | 2 | 4 | 4 | 3 | 0 | 0 | 1 | 4 | 4 | 3 | 0 | 0 |
| 52 | 3 | 5 | 5 | 4 | 0 | 0 | 2 | 5 | 5 | 5 | 1 | 0 |
| 53 | 4 | 5 | 5 | 5 | 0 | 0 | 4 | 5 | 5 | 5 | 2 | 1 |
| 54 | 4 | 5 | 5 | 5 | 0 | 0 | 4 | 5 | 5 | 5 | 2 | 0 |
| 55 | 3 | 5 | 5 | 5 | 0 | 0 | 2 | 5 | 5 | 5 | 0 | 0 |
| 56 | 4 | 5 | 5 | 5 | 0 | 0 | 5 | 5 | 5 | 5 | 2 | 1 |
| 57 | 3 | 5 | 5 | 5 | 0 | 0 | 5 | 5 | 5 | 5 | 2 | 1 |

TABLE 3-continued

| Compound No. | Preemergence application | | | | | | Postemergence application | | | | | |
|---|---|---|---|---|---|---|---|---|---|---|---|---|
| | Crab-grass | Velvet-leaf | Lambs-quarter | Smart-weed | Soy-bean | Indian corn | Crab-grass | Velvet-leaf | Lambs-quarter | Smart-weed | Soy-bean | Indian corn |
| 58 | 3 | 5 | 5 | 4 | 0 | 0 | 4 | 5 | 5 | 5 | 2 | 0 |
| 59 | 2 | 5 | 5 | 4 | 0 | 0 | 3 | 5 | 5 | 4 | 1 | 0 |
| 60 | 2 | 4 | 5 | 4 | 0 | 0 | 2 | 5 | 5 | 5 | 0 | 0 |
| 61 | 2 | 5 | 5 | 4 | 0 | 0 | 3 | 4 | 5 | 4 | 0 | 0 |
| 62 | 2 | 5 | 5 | 4 | 0 | 0 | 3 | 5 | 5 | 4 | 0 | 0 |
| 63 | 2 | 4 | 4 | 3 | 0 | 0 | 2 | 4 | 4 | 4 | 0 | 0 |
| 64 | 2 | 4 | 4 | 3 | 0 | 0 | 2 | 4 | 3 | 4 | 0 | 0 |
| 65 | 4 | 5 | 4 | 5 | 0 | 0 | 3 | 5 | 5 | 5 | 0 | 0 |
| 66 | 3 | 5 | 5 | 4 | 0 | 0 | 3 | 5 | 5 | 5 | 1 | 0 |
| 67 | 3 | 5 | 4 | 5 | 0 | 0 | 3 | 4 | 5 | 5 | 0 | 0 |
| 68 | 4 | 5 | 5 | 5 | 0 | 0 | 4 | 5 | 5 | 5 | 1 | 0 |
| 69 | 4 | 5 | 5 | 5 | 0 | 0 | 4 | 5 | 5 | 5 | 1 | 0 |
| 70 | 4 | 5 | 5 | 5 | 0 | 0 | 4 | 5 | 5 | 5 | 2 | 0 |
| 71 | 3 | 4 | 5 | 5 | 0 | 0 | 3 | 5 | 5 | 5 | 1 | 0 |
| 72 | 2 | 4 | 4 | 5 | 0 | 0 | 2 | 4 | 5 | 4 | 0 | 0 |
| 73 | 3 | 4 | 5 | 5 | 0 | 0 | 2 | 4 | 5 | 5 | 0 | 0 |
| Comparative Compound No. 1 (Note 1) | 5 | 5 | 5 | 5 | 4 | 2 | 5 | 5 | 5 | 5 | 5 | 3 |
| Comparative Compound No. 2 (Note 2) | 2 | 2 | 3 | 3 | 0 | 0 | 3 | 2 | 3 | 4 | 0 | 0 |

Note 1.
Comparative Compound No. 1:

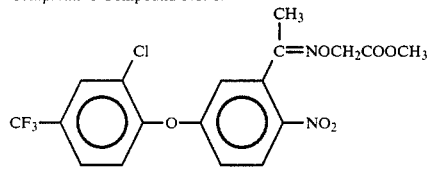

(PPG 1013)

Note 2.
Comparative Compound No. 2:

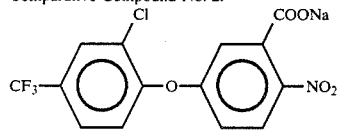

(Acifluorfen sodium)

APPLICATION EXAMPLE 2

A plowed field was partitioned into sections each having an area of 1 m². In the soil of each section were sown seeds of soybean and Indian corn for crop plants and seeds of crabgrass, lambsquarter, smartweed, velvetleaf, hemp sesbania, morningglory, jimsonweed, teaweed and cocklebur for weeds, respectively, and allowed to grow. The postemergence application was effected to the stalks and leaves when the soybean, the Indian corn and the weeds grew up to respectively 2 go 3 leaf stage, 3 to 4 leaf stage and 3 to 5 leaf stage. The herbicidal composition of the present invention was applied as follows. Using the compounds listed in Table 4, emulsifiable concentrates were prepared according to the method described in Preparation Example 2. Each of the thus prepared concentrates was diluted with 10 liters of water per each are of the upland soil, and then applied by means of a sprayer. 14 Days after the application, the degree of the herbicidal effect on the weeds was observed. 30 Days after the application, the degree of the phytotoxicity to the crop plants was observed. The results obtained are shown in Table 4. The criteria for the values indicated in Table 4 are the same as those employed in Application Example 1.

TABLE 4

| Compound No. | Dosage (g/10a) | Crab-grass | Jimson-weed | Lambs-quarter | Smart-weed | Velvet-leaf | Hemp sesbania | Morning-glory | Cockle-bur | Tea-weed | Soy-bean | Indian corn |
|---|---|---|---|---|---|---|---|---|---|---|---|---|
| 9 | 20 | 2 | 5 | 5 | 5 | 5 | 5 | 5 | 5 | 5 | 0 | 0 |
| | 10 | 2 | 5 | 5 | 5 | 5 | 5 | 4 | 5 | 5 | 0 | 0 |
| | 5 | 1 | 5 | 4 | 5 | 5 | 5 | 3 | 5 | 5 | 0 | 0 |
| | 2.5 | 0 | 5 | 4 | 4 | 5 | 5 | 2 | 3 | 4 | 0 | 0 |
| 10 | 20 | 2 | 5 | 5 | 5 | 5 | 5 | 5 | 5 | 5 | 1 | 1 |
| | 10 | 1 | 5 | 5 | 5 | 5 | 5 | 4 | 5 | 5 | 0 | 0 |
| | 5 | 1 | 5 | 3 | 5 | 5 | 5 | 3 | 5 | 4 | 0 | 0 |
| | 2.5 | 0 | 5 | 3 | 4 | 5 | 5 | 2 | 4 | 4 | 0 | 0 |

TABLE 4-continued

| Compound No. | Dosage (g/10a) | Herbicidal Activity and Phytotoxicity ||||||||||
|---|---|---|---|---|---|---|---|---|---|---|---|
| | | Crab-grass | Jimson-weed | Lambs-quarter | Smart-weed | Velvet-leaf | Hemp sesbania | Morning-glory | Cockle-bur | Tea-weed | Soy-bean | Indian corn |
| 18 | 20 | 2 | 5 | 5 | 5 | 5 | 5 | 3 | 5 | 5 | 0 | 0 |
| | 10 | 1 | 5 | 5 | 5 | 5 | 5 | 3 | 3 | 5 | 0 | 0 |
| | 5 | 0 | 5 | 4 | 4 | 5 | 5 | 2 | 3 | 4 | 0 | 0 |
| | 2.5 | 0 | 5 | 4 | 4 | 5 | 5 | 2 | 2 | 4 | 0 | 0 |
| 20 | 20 | 3 | 5 | 5 | 5 | 5 | 5 | 3 | 5 | 5 | 1 | 0 |
| | 10 | 2 | 5 | 4 | 5 | 5 | 5 | 2 | 3 | 5 | 0 | 0 |
| | 5 | 1 | 5 | 3 | 4 | 5 | 5 | 2 | 3 | 4 | 0 | 0 |
| | 2.5 | 1 | 5 | 3 | 3 | 5 | 5 | 1 | 2 | 4 | 0 | 0 |
| 36 | 20 | 2 | 5 | 5 | 5 | 5 | 5 | 3 | 4 | 5 | 0 | 0 |
| | 10 | 1 | 5 | 4 | 5 | 5 | 5 | 2 | 3 | 5 | 0 | 0 |
| | 5 | 0 | 5 | 3 | 4 | 5 | 5 | 2 | 3 | 4 | 0 | 0 |
| | 2.5 | 0 | 4 | 2 | 3 | 5 | 5 | 1 | 2 | 4 | 0 | 0 |
| 55 | 20 | 1 | 5 | 4 | 5 | 5 | 5 | 4 | 4 | 5 | 0 | 0 |
| | 10 | 1 | 5 | 3 | 5 | 5 | 5 | 3 | 4 | 4 | 0 | 0 |
| | 5 | 0 | 4 | 2 | 3 | 4 | 5 | 2 | 3 | 3 | 0 | 0 |
| | 2.5 | 0 | 3 | 1 | 2 | 4 | 4 | 0 | 3 | 3 | 0 | 0 |
| 56 | 20 | 1 | 5 | 4 | 5 | 5 | 5 | 4 | 5 | 5 | 1 | 0 |
| | 10 | 1 | 5 | 4 | 5 | 5 | 5 | 4 | 4 | 5 | 1 | 0 |
| | 5 | 0 | 5 | 3 | 5 | 5 | 5 | 3 | 4 | 4 | 0 | 0 |
| | 2.5 | 0 | 5 | 3 | 5 | 5 | 5 | 3 | 4 | 4 | 0 | 0 |
| 57 | 20 | 2 | 5 | 5 | 5 | 5 | 5 | 5 | 4 | 5 | 1 | 0 |
| | 10 | 2 | 5 | 4 | 5 | 5 | 5 | 4 | 4 | 5 | 0 | 0 |
| | 5 | 1 | 5 | 4 | 5 | 5 | 5 | 3 | 4 | 4 | 0 | 0 |
| | 2.5 | 1 | 5 | 3 | 4 | 4 | 5 | 3 | 3 | 3 | 0 | 0 |
| Comparative Compound No. 1 (Note 1) | 20 | 3 | 4 | 5 | 5 | 3 | 5 | 5 | 2 | 4 | 0 | 1 |
| | 10 | 3 | 3 | 4 | 5 | 2 | 5 | 5 | 1 | 3 | 0 | 0 |
| | 5 | 2 | 3 | 3 | 4 | 1 | 5 | 4 | 1 | 2 | 0 | 0 |
| | 2.5 | 2 | 2 | 2 | 4 | 1 | 5 | 4 | 1 | 2 | 0 | 0 |
| Comparative Compound No. 2 (Note 2) | 20 | 2 | 5 | 4 | 5 | 4 | 5 | 5 | 4 | 4 | 0 | 0 |
| | 10 | 2 | 5 | 4 | 5 | 2 | 5 | 4 | 4 | 3 | 0 | 0 |
| | 5 | 1 | 4 | 3 | 4 | 1 | 5 | 4 | 3 | 3 | 0 | 0 |
| | 2.5 | 1 | 3 | 3 | 4 | 1 | 5 | 3 | 3 | 2 | 0 | 2 |
| Comparative Compound No. 3 (Note 3) | 10 | 3 | 5 | 5 | 5 | 5 | 5 | 5 | 5 | 5 | 3 | 2 |
| | 5 | 2 | 5 | 5 | 5 | 5 | 5 | 4 | 5 | 5 | 3 | 1 |
| | 2.5 | 1 | 5 | 4 | 5 | 4 | 5 | 3 | 4 | 5 | 2 | 0 |
| | 1.25 | 1 | 4 | 2 | 4 | 4 | 5 | 2 | 3 | 4 | 1 | 0 |

Note 1.
Comparative Compound No. 1:

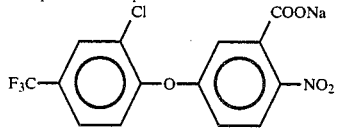

(Acifluorfen sodium)

Note 2.
Comparative Compound No. 2:

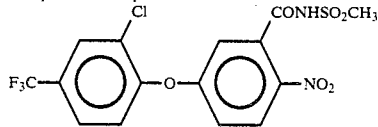

(Fomesafen)

Note 3.
Comparative Compound No. 3:

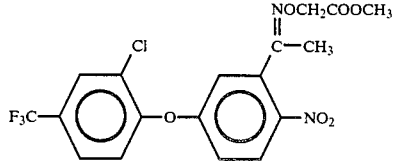

(PPG-1013)

APPLICATION EXAMPLE 3

Pots each having a surface area of 1/5000 a were packed with paddy field soil in a greenhouse. Seeds of barnyardgrass and monochria, seeds of broad-leaved annual weeds, toothcup and false pimpernel, and seeds of perennial weeds, "Hotarui" (*Scirpus juncoides*), were mixed with dry paddy field soil and incorporated into the surface soil. Further, as the perennial weeds, tubers of arrowhead and flat sedge were transplanted.

Rice seedlings of 3 leaf stage were transplanted at a depth of 2 to 3 cm from the surface soil. Using the compounds listed in Table 5, emulsifiable concentrates were prepared according to the method described in Preparation Example 2. Each of the thus prepared concentrates was diluted with water and dropwise applied by means of a pipette when the barnyardgrass grew up to 0.5 to 1 leaf stage. 21 Days after the application, phytotoxicity to rice plants and herbicidal effects on weeds were observed. The results obtained are shown in Table 5. The criteria for the values indicated in Table 5 are the same as those employed in Application Example 1.

TABLE 5

| Compound No. | Dosage (g/10a) | Herbicidal Effect | | | | | | Phytotoxicity to rice plant |
|---|---|---|---|---|---|---|---|---|
| | | Barnyardgrass | Monochoria | Broadleaved weeds | Hotarui (*Scirpus juncoides*) | Arrowhead | Flat sedge | |
| 1 | 30 | 5 | 5 | 5 | 5 | 4 | 2 | 0 |
|   | 15 | 4 | 4 | 5 | 5 | 3 | 1 | 0 |
| 3 | 30 | 5 | 5 | 5 | 5 | 4 | 5 | 2 |
|   | 15 | 5 | 5 | 5 | 5 | 3 | 4 | 1 |
| 6 | 30 | 5 | 5 | 5 | 5 | 4 | 4 | 1 |
|   | 15 | 4 | 5 | 5 | 5 | 3 | 2 | 0 |
| 9 | 30 | 5 | 5 | 5 | 5 | 4 | 5 | 2 |
|   | 15 | 5 | 5 | 5 | 5 | 3 | 4 | 1 |
| 10 | 30 | 5 | 5 | 5 | 5 | 4 | 5 | 2 |
|   | 15 | 5 | 5 | 5 | 5 | 3 | 4 | 1 |
| 14 | 30 | 5 | 5 | 5 | 5 | 4 | 4 | 1 |
|   | 15 | 4 | 5 | 5 | 5 | 3 | 3 | 0 |
| 15 | 60 | 5 | 5 | 5 | 5 | 3 | 2 | 2 |
|   | 30 | 5 | 5 | 5 | 4 | 3 | 2 | 1 |
| 17 | 60 | 5 | 5 | 5 | 5 | 4 | 4 | 2 |
|   | 30 | 5 | 5 | 5 | 5 | 3 | 3 | 1 |
| 19 | 60 | 5 | 5 | 5 | 4 | 2 | 1 | 0 |
|   | 30 | 4 | 4 | 5 | 3 | 1 | 1 | 0 |
| 20 | 60 | 5 | 5 | 5 | 4 | 3 | 1 | 0 |
|   | 30 | 4 | 4 | 5 | 3 | 2 | 1 | 0 |
| 21 | 60 | 5 | 5 | 5 | 5 | 3 | 2 | 1 |
|   | 30 | 5 | 5 | 5 | 4 | 2 | 1 | 0 |
| 23 | 60 | 5 | 5 | 5 | 5 | 3 | 4 | 1 |
|   | 30 | 5 | 5 | 5 | 4 | 2 | 3 | 0 |
| 24 | 60 | 5 | 5 | 5 | 5 | 4 | 4 | 2 |
|   | 30 | 5 | 5 | 5 | 4 | 3 | 4 | 1 |
| 27 | 60 | 5 | 5 | 5 | 5 | 4 | 3 | 1 |
|   | 30 | 5 | 5 | 5 | 4 | 3 | 2 | 1 |
| 29 | 60 | 5 | 5 | 5 | 5 | 4 | 4 | 1 |
|   | 30 | 5 | 5 | 5 | 4 | 3 | 2 | 0 |
| 30 | 60 | 5 | 5 | 5 | 4 | 3 | 3 | 1 |
|   | 30 | 4 | 5 | 5 | 3 | 2 | 2 | 0 |
| 31 | 60 | 5 | 5 | 5 | 5 | 4 | 3 | 1 |
|   | 40 | 5 | 5 | 5 | 4 | 3 | 2 | 1 |
| 34 | 60 | 5 | 5 | 5 | 4 | 3 | 2 | 1 |
|   | 40 | 5 | 5 | 5 | 3 | 2 | 1 | 0 |
| 35 | 60 | 5 | 5 | 5 | 4 | 3 | 2 | 0 |
|   | 40 | 4 | 4 | 5 | 3 | 2 | 1 | 0 |
| 37 | 60 | 5 | 5 | 5 | 4 | 2 | 2 | 0 |
|   | 40 | 4 | 5 | 5 | 3 | 1 | 1 | 0 |
| 38 | 60 | 5 | 5 | 5 | 4 | 3 | 4 | 1 |
|   | 40 | 4 | 4 | 5 | 3 | 1. | 3 | 0 |
| 40 | 60 | 5 | 5 | 5 | 4 | 3 | 3 | 0 |
|   | 40 | 4 | 5 | 5 | 3 | 2 | 1 | 0 |
| 41 | 60 | 5 | 5 | 5 | 4 | 3 | 4 | 1 |
|   | 40 | 4 | 5 | 5 | 3 | 2 | 3 | 0 |
| 43 | 60 | 5 | 5 | 5 | 4 | 3 | 3 | 0 |
|   | 40 | 4 | 4 | 5 | 3 | 2 | 1 | 0 |
| 44 | 60 | 5 | 5 | 5 | 4 | 3 | 3 | 1 |
|   | 30 | 5 | 5 | 5 | 3 | 2 | 1 | 0 |
| 45 | 60 | 5 | 5 | 5 | 5 | 3 | 4 | 2 |
|   | 30 | 5 | 5 | 5 | 4 | 2 | 3 | 1 |
| 47 | 60 | 5 | 5 | 5 | 4 | 3 | 2 | 1 |
|   | 30 | 4 | 4 | 5 | 3 | 2 | 1 | 0 |
| 49 | 60 | 5 | 5 | 5 | 5 | 4 | 3 | 2 |
|   | 30 | 5 | 5 | 5 | 5 | 3 | 2 | 1 |
| 50 | 60 | 5 | 5 | 5 | 5 | 4 | 3 | 2 |
|   | 30 | 5 | 5 | 5 | 4 | 3 | 2 | 1 |
| 51 | 30 | 4 | 5 | 5 | 5 | 2 | 1 | 0 |
|   | 15 | 4 | 4 | 5 | 5 | 2 | 1 | 0 |
| 53 | 60 | 5 | 5 | 5 | 5 | 4 | 3 | 1 |
|   | 30 | 4 | 5 | 5 | 4 | 3 | 3 | 0 |
| 54 | 60 | 5 | 5 | 5 | 5 | 4 | 3 | 0 |
|   | 30 | 4 | 5 | 5 | 3 | 3 | 2 | 0 |
| 56 | 60 | 5 | 5 | 5 | 5 | 2 | 2 | 0 |
|   | 30 | 4 | 5 | 5 | 4 | 1 | 0 | 0 |
| 61 | 60 | 5 | 5 | 5 | 5 | 3 | 3 | 1 |
|   | 30 | 5 | 5 | 5 | 4 | 1 | 2 | 1 |
| 63 | 60 | 5 | 5 | 5 | 5 | 2 | 3 | 1 |
|   | 30 | 4 | 5 | 5 | 4 | 2 | 2 | 0 |
| 65 | 60 | 5 | 5 | 5 | 5 | 3 | 2 | 1 |
|   | 30 | 5 | 5 | 5 | 5 | 2 | 1 | 1 |
| 72 | 60 | 5 | 5 | 5 | 5 | 3 | 2 | 1 |
|   | 30 | 4 | 5 | 5 | 4 | 2 | 1 | 0 |

TABLE 5-continued

| Compound No. | Dosage (g/10a) | Herbicidal Effect | | | | | | Phytotoxicity to rice plant |
|---|---|---|---|---|---|---|---|---|
| | | Barnyardgrass | Monochoria | Broadleaved weeds | Hotarui (*Scirpus juncoides*) | Arrowhead | Flat sedge | |
| Comparative Compound No. 1 (Note 1) | 150 | 2 | 3 | 5 | 4 | 2 | 2 | 0 |
| | 75 | 1 | 2 | 5 | 3 | 1 | 1 | 0 |
| Comparative Compound No. 2 (Note 2) | 150 | 2 | 5 | 5 | 4 | 3 | 2 | 0 |
| | 75 | 1 | 2 | 5 | 3 | 1 | 1 | 0 |
| Comparative Compound No. 3 (Note 3) | 30 | 5 | 5 | 5 | 5 | 5 | 5 | 5 |
| | 15 | 5 | 5 | 5 | 5 | 4 | 4 | 4 |

Note 1. Comparative Compound No. 1

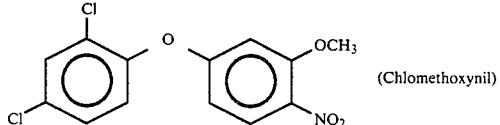

(Chlomethoxynil)

Note 2. Comparative Compound No. 2

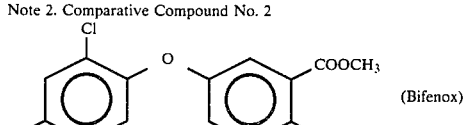

(Bifenox)

Note 3. Comparative Compound No. 3

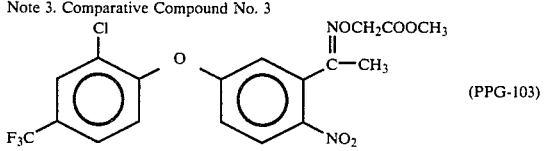

(PPG-103)

What is claimed is:

1. A compound represented by the formula

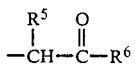

(I)

wherein $R^1$ represents a methyl group or $$-\overset{R^3}{\underset{|}{CH}}-\overset{O}{\underset{\|}{C}}-A-R^4$$

in which

A represents an oxygen atom or a sulfur atom, $R^3$ represents a hydrogen atom or a methyl group, and $R^4$ represents a hydrogen atom, an alkyl group having 1 to 4 carbon atoms, an alkenyl group having 3 to 6 carbon atoms, an alkynyl group having 3 to 6 carbon atoms, or an alkyl group having 1 to 4 carbon atoms and substituted with a halogen atom, an alkoxy group having 1 to 3 carbon atoms or a carboalkoxy group having 2 to 4 carbon atoms; and Y represents an oxygen atom or $=$N-O-$R^2$ in which $R^2$ represents a hydrogen atom, an alkyl group having 1 to 3 carbon atoms or $$-\overset{R^5}{\underset{|}{CH}}-\overset{O}{\underset{\|}{C}}-R^6$$

in which $R^5$ represents a hydrogen atom or a methyl group, and $R^6$ represents —$BR^7$ or

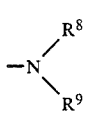

in which

B represents an oxygen atom or a sulfur atom, $R^7$ represents a hydrogen atom, an alkyl group having 1 to 4 carbon atoms, an alkenyl group having 3 to 6 carbon atoms, an alkynyl group having 3 to 6 carbon atoms, an unsubstituted phenyl group, a phenyl group substituted with a chlorine atom, a methyl group or a methoxy group, an alkyl group having 1 to 4 carbon atoms and substituted with a halogen atom or an alkoxy group having 1 to 3 carbon atoms, an alkali metal, an alkaline earth metal, an ammonium group, an ammonium group substituted with an alkyl group having 1 to 4 carbon atoms, or

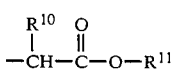

in which $R^{10}$ represents a hydrogen atom or a methyl group, and $R^{11}$ represents an alkyl group having 1 to 3 carbon atoms, and $R^8$ and $R^9$ are identical or different and each independently represents a hydrogen atom, an alkyl group having 1 to 3 carbon atoms, an alkynyl group having 3 to 6 atoms, or an alkoxy gorup having 1 to 3 carbon atoms.

2. A compound according to claim 1, wherein $R^1$ represents a methyl group, $R^5$ represents a hydrogen atom, B represents an oxygen atom, and $R^7$ represents an alkyl group having 1 to 3 carbon atoms.

3. A compound according to claim 1, wherein $R^1$ represents a methyl group, $R^5$ represents a hydrogen atom, B represents an oxygen atom, and $R^7$ is a member selected from the group consisting of a hydrogen atom, an unsubstituted phenyl group, an alkyl group having 1 to 4 carbon atoms and substituted with a chlorine atom, and an alkali metal.

4. A compound according to claim 1, wherein $R^1$ represents a methyl group, B represents a sulfur atom, and $R^7$ is a member selected from the group consisting of an alkyl group having 1 to 3 carbon atoms and an alkyl group having 1 to 4 carbon atoms and substituted with a carboalkoxy group having 2 or 3 carbon atoms.

5. A compound according to claim 1, wherein $R^1$ represents a methyl group, and $R^8$ and $R^9$ are identical or different and each independently represent a member selected from the group consisting of a hydrogen atom, a methyl group and a methoxy group.

6. A compound according to claim 1, wherein Y and A represent an oxygen atom, and $R^4$ represents an alkyl group having 1 to 3 carbon atoms.

7. A compound according to claim 1, wherein Y represents an oxygen atom, $R^3$ represents a methyl group, A represents an oxygen atom, and $R^4$ is a member selected from the group consisting of a propargyl group and an alkyl group having 2 or 3 carbon atoms and substituted with a chlorine atom or a carboalkoxy group having 2 or 3 carbon atoms.

8. 5-(2-chloro-4-trifluoromethylphenoxy)-2-nitro-α-methoxyacetophenone oxime-O-(acetic acid, methyl ester).

9. 5-(2-chloro-4-trifluoromethylphenoxy)-2-nitro-α-methoxyacetophenone oxime-O-(acetic acid, ethyl ester).

10. 5-(2-chloro-4-trifluoromethylphenoxy)-2-nitro-α-methoxyacetophenone oxime-O-(acetic acid, 2-chloroethyl ester).

11. 5-(2-chloro-4-trifluoromethylphenoxy)-2-nitro-α-methoxyacetophenone oxime-O-(acetic acid, phenyl ester).

12. A compound according to claim 1 selected from the group consisting of:
5-(2-chloro-4-trifluoromethylphenoxy)-2-nitro-α-methoxyacetophenone oxime-O-(thioacetic acid, S-ethyl ester),
5-(2-chloro-4-trifluoromethylphenoxy)-2-nitro-α-methoxyacetophenone oxime-O-(acetic acid, N-methyl-N-methoxyamide),
5-(2-chloro-4-trifluoromethylphenoxy)-2-nitro-α-methoxyacetophenone oxime-O-(2-propionamide), and
5-(2-chloro-4-trifluoromethylphenoxy)-2-nitro-α-methoxyacetophenone oxime-O-(2-thiopropionic acid, S-methoxycarbonylmethyl ester).

13. A compound according to claim 1 selected from the group consisting of:
5-(2-chloro-4-trifluoromethylphenoxy)-2-nitro-α-methoxyacetophenone oxime-O-(acetic acid),
5-(2-chloro-4-trifluoromethylphenoxy)-2-nitro-α-methoxyacetophenone oxime-O-(2-propionic acid),
agronomically soluble sodium and potassium salts of 5-(2-chloro-4-trifluoromethylphenoxy)-2-nitro-α-methoxyacetophenone oxime-O-(acetic acid), and
agronomically soluble sodium and potassium salts of 5-(2-chloro-4-trifluoromethylphenoxy)-2-nitro-α-methoxyacetophenone oxime-O-(2-propionic acid).

14. A compound according to claim 1 selected from the group consisting of:
ethyl 2-nitro-5-(2-chloro-4-trifluoromethylphenoxy)-phenacyloxyacetate,
methyl 2-[2-nitro-5-(2'-chloro-4'-trifluoromethylphenoxy)phenacyloxy]propionate,
ethyl 2-[2-nitro-5(2'-chloro-4'-trifluoromethylphenoxy)phenacyloxy]propionate,
n-propyl 2-[2-chloro-5-(2'-chloro-4'-trifluoromethylphenoxy)phenacyloxy]propionate,
2-chloroethyl 2-[2-nitro-5-(2'-chloro-4'-trifluoromethylphenoxy)phenacyloxy]propionate,
propargyl 2-[2-nitro-5-(2'-chloro-4'-trifluoromethylphenoxy)phenacyloxy]propionate, and
methyl 2-[2-[2'-nitro-5'-(2''-chloro-4''-trifluoromethylphenoxy)phenacyloxy]propionyloxy]propionate.

15. A compound represented by the formula

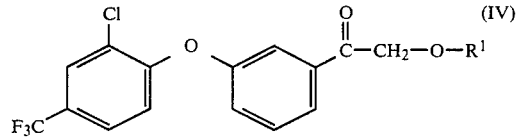

wherein
$R^1$ represents a methyl group or

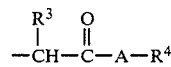

in which
A represents an oxygen atom or a sulfur atom,
$R^3$ represents a hydrogen atom or a methyl group, and
$R^4$ represents a hydrogen atom, an alkyl group having 1 to 4 carbon atoms, an alkenyl group having 3 to 6 carbon atoms, an alkynyl group having 3 to 6 carbon atoms, or an alkyl group having 1 to 4 carbon atoms and substituted with a halogen atom, an alkoxy group having 1 to 3 carbon atoms or a carboalkoxy group having 2 to 4 carbon atoms.

16. A compound represented by the formula

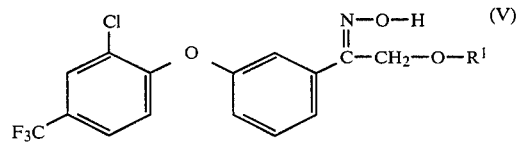

wherein
$R^1$ represents a methyl group or

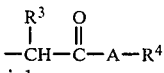

in which
A represents an oxygen atom or a sulfur atom,
R³ represents a hydrogen atom or a methyl group, and
R⁴ represents a hydrogen atom, an alkyl group having 1 to 4 carbon atoms, an alkenyl group having 3 to 6 carbon atoms, an alkynyl group having 3 to 6 carbon atoms, or an alkyl group having 1 to 4 carbon atoms and substituted with a halogen atom, an alkoxy group having 1 to 3 carbon atoms or a carboalkoxy group having 2 to 4 carbon atoms.

17. A compound represented by the formula

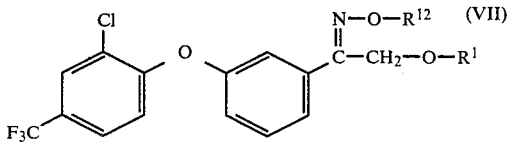

wherein
R¹ represents a methyl group or

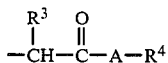

in which
A represents an oxygen atom or a sulfur atom,
R³ represents a hydrogen atom or a methyl group, and
R⁴ represents a hydrogen atom, an alkyl group having 1 to 4 carbon atoms, an alkenyl group having 3 to 6 carbon atoms, an alkynyl group having 3 to 6 carbon atoms, or an alkyl group having 1 to 4 carbon atoms and substituted with a halogen atom, an alkoxy group having 1 to 3 carbon atoms or a carboalkoxy group having 2 to 4 carbon atoms; and
R¹² represents an alkyl group having 1 to 3 carbon atoms or

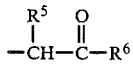

in which
R⁵ represents a hydrogen atom or a methyl group, and
R⁶ represents —BR⁷ or

in which
B represents an oxygen atom or a sulfur atom,
R⁷ represents a hydrogen atom, an alkyl group having 1 to 4 carbon atoms, an alkenyl group having 3 to 6 carbon atoms, an alkynyl group having 3 to 6 carbon atoms, an unsubstituted phenyl group, a phenyl group substituted with a chlorine atom, a methyl group or a methoxy group, an alkyl group having 1 to 4 carbon atoms and substituted with a halogen atom or an alkoxy group having 1 to 3 carbon atoms, an alkali metal, an alkaline earth metal, an ammonium group, an ammonium group substituted with an alkyl group having 1 to 4 carbon atoms, or

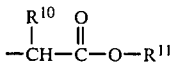

in which
R¹⁰ represents a hydrogen atom or a methyl group, and
R¹¹ represents an alkyl group having 1 to 3 carbon atoms, and
R⁸ and R⁹ are identical or different and each independently represents a hydrogen atom, an alkyl group having 1 to 3 carbon atoms, an alkynyl group having 3 to 6 carbon atoms, or an alkoxy group having 1 to 3 carbon atoms.

18. A herbicidal composition which comprises as an active ingredient a herbicidally effective amount of a compound represented by the formula

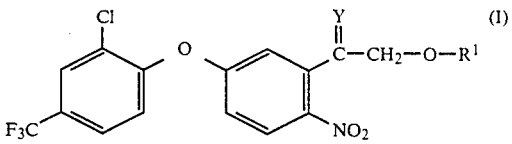

wherein
R¹ represents a methyl group or

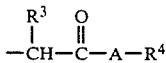

in which
A represents an oxygen atom or a sulfur atom,
R³ represents a hydrogen atom or a methyl group, and
R⁴ represents a hydrogen atom, an alkyl group having 1 to 4 carbon atoms, an alkenyl group having 3 to 6 carbon atoms, an alkynyl group having 3 to 6 carbon atoms, or an alkyl group having 1 to 4 carbon atoms and substituted with a halogen atom, an alkoxy group having 1 to 3 carbon atoms or a carboalkoxy group having 2 to 4 carbon atoms; and
Y represents an oxygen atom or =N-O-R²
in which
R² represents a hydrogen atom, an alkyl group having 1 to 3 carbon atoms or

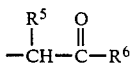

in which
R⁵ represents a hydrogen atom or a methyl group, and
R⁶ represents —BR⁷ or

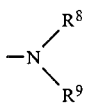

in which

B represents an oxygen atom or a sulfur atom,

R$^7$ represents a hydrogen atom, an alkyl group having 1 to 4 carbon atoms, an alkenyl group having 3 to 6 carbon atoms, an alkynyl group having 3 to 6 carbon atoms, an unsubstituted phenyl group, a phenyl group substituted with a chlorine atom, a methyl group or a methoxy group, an alkyl group having 1 to 4 carbon atoms and substituted with a halogen atom or an alkoxy group having 1 to 3 carbon atoms, an alkali metal, an alkaline earth metal, an ammonium group, an ammonium group substituted with an alkyl group having 1 to 4 carbon atoms, or

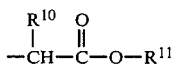

in which

R$^{10}$ represents a hydrogen atom or a methyl group, and

R$^{11}$ represents an alkyl group having 1 to 3 carbon atoms, and

R$^8$ and R$^9$ are identical or different and each independently represents a hydrogen atom, an alkyl group having 1 to 3 carbon atoms, an alkynyl group having 3 to 6 atoms, or an alkoxy group having 1 to 3 carbon atoms.

19. A herbicidal composition according to claim 18, wherein R$^1$ represents a methyl group, R$^5$ represents a hydrogen atom, B represents an oxygen atom, and R$^7$ represents an alkyl group having 1 to 3 carbon atoms.

20. A herbicidal composition according to claim 18, wherein R$^1$ represents a methyl group, R$^5$ represents a hydrogen atom, B represents an oxygen atom, and R$^7$ is a member selected from the group consisting of a hydrogen atom, an unsubstituted phenyl group, an alkyl group having 1 to 4 carbon atoms and substituted with a chlorine atom, and an alkali metal.

21. A herbicidal composition according to claim 18, wherein R$^1$ represents a methyl group, B represents a sulfur atom, and R$^7$ is a member selected from the group consisting of an alkyl group having 1 to 3 carbon atoms and an alkyl group having 1 to 4 carbon atoms and substituted with a carboalkoxy group having 2 or 3 carbon atoms.

22. A herbicidal composition according to claim 18, wherein R$^1$ represents a methyl group, and R$^8$ and R$^9$ are identical or different and each independently represent a member selected from the group consisting of a hydrogen atom, a methyl group and a methoxy group.

23. A herbicidal composition according to claim 18, wherein Y and A represent an oxygen atom, and R$^4$ represents an alkyl group having 1 to 3 carbon atoms.

24. A herbicidal composition according to claim 18, wherein Y represents an oxygen atom, R$^3$ represents a methyl group, A represents an oxygen atom, and R$^4$ is a member selected from the group consisting of a propargyl group and an alkyl group having 2 or 3 carbon atoms and substituted with a chlorine atom or a carboalkoxy group having 2 or 3 carbon atoms.

25. A herbicidal composition according to claim 18, wherein the active ingredient is 5-(2-chloro-4-trifluoromethylphenoxy)-2-nitro-α-methoxyacetophenone oxime-O-(acetic acid, methyl ester).

26. A herbicidal composition according to claim 18, wherein the active ingredient is 5-(2-chloro-4-trifluoromethylphenoxy)-2-nitro-α-methoxyacetophenone oxime-O-(acetic acid, ethyl ester).

27. A herbicidal composition according to claim 18, wherein the active ingredient is 5-(2-chloro-4-trifluoromethylphenoxy)-2-nitro-α-methoxyacetophenone oxime-O-(acetic acid, 2-chloroethyl ester).

28. A herbicidal composition according to claim 18, wherein the active ingredient is 5-(2-chloro-4-trifluoromethylphenoxy)-2-nitro-α-methoxyacetophenone oxime-O-(acetic acid, phenyl ester).

29. A herbicidal composition according to claim 18, wherein the active ingredient is at least one member selected from the group consisting of:

5-(2-chloro-4-trifluoromethylphenoxy)-2-nitro-α-methoxyacetophenone oxime-O-(thioacetic acid, S-ethyl ester), 5-(2-chloro-4-trifluoromethylphenoxy)-2-nitro-α-methoxyacetophenone oxime-O-(acetic acid, N-methyl-N-methoxyamide), 5-(2-chloro-4-trifluoromethylphenoxy)-2-nitro-α-methoxyacetophenone oxime-O-(2-propionamide), and 5-(2-chloro-4-trifluoromethylphenoxy)-2-nitro-α-methoxyacetophenone oxime-O-(2-thiopropionic acid, S-methoxycarbonylmethyl ester).

30. A herbicidal composition according to claim 18, wherein the active ingredient is at least one member selected from the group consisting of:

5-(2-chloro-4-trifluoromethylphenoxy)-2-nitro-α-methoxyacetophenone oxime-O-(acetic acid), 5-(2-chloro-4-trifluoromethylphenoxy)-2-nitro-α-methoxyacetophenone oxime-O-(2-propionic acid), agronomically soluble sodium and potassium salts of 5-(2-chloro-4-trifluoromethylphenoxy)-2-nitro-α-methoxyacetophenone oxime-O-(acetic acid), and agronomically soluble sodium and potassium salts of 5-(2-chloro-4-trifluoromethylphenoxy)-2-nitro-α-methoxyacetophenone oxime-O-(2-propionic acid).

31. A herbicidal composition according to claim 18, wherein the active ingredient is at least one member selected from the group consisting of:

ethyl 2-nitro-5-(2-chloro-4-trifluoromethylphenoxy)-phenacyloxyacetate, methyl 2-[2-nitro-5-(2'-chloro-4'-trifluoromethylphenoxy)phenacyloxy]propionate, ethyl 2-[2-nitro-5-(2'-chloro-4'-trifluoromethylphenoxy)phenacyloxy]propionate, n-propyl 2-[2-chloro-5-(2'-chloro-4'-trifluoromethylphenoxy)phenacyloxy]propionate, 2-chloroethyl 2-[2-nitro-5-(2'-chloro-4'-trifluoromethylphenoxy)phenacyloxy]propionate, propargyl 2-[2-nitro-5-(2'-chloro-4'-trifluoromethylphenoxy)phenacyloxy]propionate, and methyl 2-[2-[2'-nitro-5'-(2''-chloro-4''-trifluoromethylphenoxy)phenacyloxy]propionate.

32. A method for the destruction of undesirable weeds, which comprises applying to said weeds a herbicidally effective amount of a compound represented by the formula

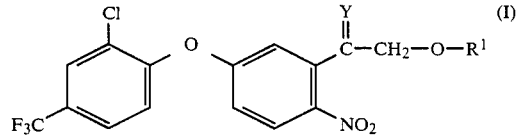

wherein $R^1$ represents a methyl group or

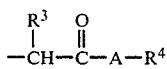

in which

A represents an oxygen atom or a sulfur atom, $R^3$ represents a hydrogen atom or a methyl group, and $R^4$ represents a hydrogen atom, an alkyl group having 1 to 4 carbon atoms, an alkenyl group having 3 to 6 carbon atoms, an alkynyl group having 3 to 6 carbon atoms, or an alkyl group having 1 to 4 carbon atoms and substituted with a halogen atom, an alkoxy group having 1 to 3 carbon atoms or a carboalkoxy group having 2 to 4 carbon atoms; and Y represents an oxygen atom or $=$N-O-$R^2$ in which $R^2$ represents a hydrogen atom, an alkyl group having 1 to 3 carbon atoms or

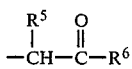

in which $R^5$ represents a hydrogen atom or a methyl group, and $R^6$ represents —B$R^7$ or

in which

B represents an oxygen atom or a sulfur atom, $R^7$ represents a hydrogen atom, an alkyl group having 1 to 4 carbon atoms, an alkenyl group having 3 to 6 carbon atoms, an alkynyl group having 3 to 6 carbon atoms, an unsubstituted phenyl group, a phenyl group substituted with a chlorine atom, a methyl group or a methoxy group, an alkyl group having 1 to 4 carbon atoms and substituted with a halogen atom or an alkoxy group having 1 to 3 carbon atoms, an alkali metal, an alkaline earth metal, an ammonium group, an ammonium group substituted with an alkyl group having 1 to 4 carbon atoms, or

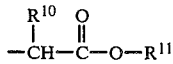

in which $R^{10}$ represents a hydrogen atom or a methyl group, and $R^{11}$ represents an alkyl group having 1 to 3 carbon atoms, and $R^8$ and $R^9$ are identical or different and each independently represents a hydrogen atom, an alkyl group having 1 to 3 carbon atoms, an alkynyl group having 3 to 6 atoms, or an alkoxy group having 1 to 3 carbon atoms.

33. A method according to claim 32, wherein $R^1$ represents a methyl group, $R^5$ represents a hydrogen atom, B represents an oxygen atom, and $R^7$ represents an alkyl group having 1 to 3 carbon atoms.

34. A method according to claim 32, wherein $R^1$ represents a methyl group, $R^5$ represents a hydrogen atom, B represents an oxygen atom, and $R^7$ is a member selected from the group consisting of a hydrogen atom, an unsubstituted phenyl group, an alkyl group having 1 to 4 carbon atoms and substituted with a chlorine atom, and an alkali metal.

35. A method according to claim 32, wherein $R^1$ represents a methyl group, B represents a sulfur atom, and $R^7$ is a member selected from the group consisting of an alkyl group having 1 to 3 carbon atoms and an alkyl group having 1 to 4 carbon atoms and substituted with a carboalkoxy group having 2 or 3 carbon atoms.

36. A method according to claim 32, wherein $R^1$ represents a methyl group, and $R^8$ and $R^9$ are identical or different and each independently represent a member selected from the group consisting of a hydrogen atom, a methyl group and methoxy group.

37. A method according to claim 32, wherein Y and A represent an oxygen atom, and $R^4$ represents an alkyl group having 1 to 3 carbon atoms.

38. A method according to claim 32, wherein Y represents an oxygen atom, $R^3$ represents a methyl group, A represents an oxygen atom, and $R^4$ is a member selected from the group consisting of a propargyl group and an alkyl group having 2 or 3 carbon atoms and substituted with a chlorine atom or a carboalkoxy group having 2 or 3 carbon atoms.

39. A method according to claim 36, wherein the compound is 5-(2-chloro-4-trifluoromethylphenoxy)-2-nitro-α-methoxyacetophenone oxime-O-(acetic acid, methyl ester).

40. A method according to claim 32, wherein the compound is 5-(2-chloro-4-trifluoromethylphenoxy)-2-nitro-α-methoxyacetophenone oxime-O-(acetic acid, ethyl ester).

41. A method according to claim 32, wherein the compound is 5-(2-chloro-4-trifluoromethylphenoxy)-2-nitro-α-methoxyacetophenone oxime-O-(acetic acid, 2-chloroethyl ester).

42. A method according to claim 32, wherein the compound is 5-(2-chloro-4-trifluoromethylphenoxy)-2-nitro-α-methoxyacetophenone oxime-O-(acetic acid, phenyl ester).

43. A method according to claim 32, wherein the compound is at least one member selected from the group consisting of:

5-(2-chloro-4-trifluoromethylphenoxy)-2-nitro-α-methoxyacetophenone oxime-O-(thioacetic acid, S-ethyl ester), 5-(2-chloro-4-trifluoromethylphenoxy)-2-nitro-α-methoxyacetophenone oxime-O-(acetic acid, N-methyl-N-methoxyamide), 5-(2-chloro-4-trifluoromethylphenoxy)-2-nitro-α-methoxyacetophenone oxime-O-(2-propionamide), and 5-(2-chloro-4-trifluoromethylphenoxy)-2-nitro-α-methoxyacetophenone oxime-O-(2-thiopropionic acid, S-methoxycarbonylmethyl ester).

44. A method according to claim 36, wherein the compound is at least one member selected from the group consisting of:

5-(2-chloro-4-trifluoromethylphenoxy)-2-nitro-α-methoxyacetophenone oxime-O-(acetic acid), 5-(2-chloro-4-trifluoromethylphenoxy)-2-nitro-α-methoxyacetophenone oxime-O-(2-propionic acid), agronomically soluble sodium and potassium salts of 5-(2-chloro-4-trifluoromethylphenoxy)-2-nitro-α-methoxyacetophenone oxime-O-(acetic acid), and
agronomically soluble sodium and potassium salts of 5-(2-chloro-4-trifluoromethylphenoxy)-2-nitro-α-methoxyacetophenone oxime-O-(2-propionic acid).

45. A method according to claim 32, wherein the compound is at least one member selected from the group consisting of:
ethyl 2-nitro-5-(2-chloro-4-trifluoromethylphenoxy)-phenacyloxyacetate,
methyl 2-[2-nitro-5-(2'-chloro-4'-trifluoromethylphenoxy)phenacyloxy] propionate,
ethyl 2-[2-nitro-5-(2'-chloro-4'-trifluoromethylphenoxy)phenacyloxy]propionate,
n-propyl 2-[2-chloro-5-(2'-chloro-4'-trifluoromethylphenoxy)phenacyloxy]propionate,
2-chloroethyl 2-[2-nitro-5-(2'-chloro-4'-trifluoromethylphenoxy)phenacyloxy]propionate,
propargyl 2-[2-nitro-5-(2'-chloro-4'-trifluoromethylphenoxy)phenacyloxy]propionate, and
methyl 2-[2-[2'-nitro-5'-(2''-chloro-4''-trifluoromethylphenoxy)phenacyloxy]propionyloxy]propionate.

* * * * *